United States Patent [19]
Klessig et al.

[11] Patent Number: 5,977,442
[45] Date of Patent: Nov. 2, 1999

[54] SALICYLIC ACID INDUCED MAP KINASE AND ITS USE FOR ENHANCED DISEASE RESISTANCE IN PLANTS

[75] Inventors: Daniel F. Klessig, Bridgewater; Shugun Zhang, Piscataway, both of N.J.

[73] Assignee: Rutgers, The State University of New Jersey, New Brunswick, N.J.

[21] Appl. No.: 08/837,593

[22] Filed: Apr. 21, 1997

Related U.S. Application Data

[60] Provisional application No. 60/029,805, Oct. 25, 1996.
[51] Int. Cl.$^6$ .............................. C12N 15/56; C12N 9/42; C12N 5/10
[52] U.S. Cl. .................... 800/301; 536/23.1; 536/23.2; 536/24.3; 536/24.33; 435/320.1; 435/419; 435/194
[58] Field of Search ................... 536/23.1, 23.2, 536/24.3, 24.33; 435/320.1, 419, 194; 800/205, 301

[56] References Cited

PUBLICATIONS

Chen, Z., Silva, H., & Klessig, D. F. (1993) Science 262, 1883–1886.
Conrath, U., Chen, Z., Ricigliano, J. R., & Klessig, D. F. (1995) Proc. Natl. Acad. Sci. USA 92, 7143–7147.
Conrath, U., Silva, H., & Klessig, D. F. (1997) Plant J., 11, 747–757.
Dempsey, D. A., & Klessig, D. F. (1995) Bull. Inst. Pasteur 93, 167–186.
Duerr, B., Gawienowski, M., Ropp, T., & Jacobs, T. (1993) Plant Cell 5, 87–96.
Dunigan, D, D, & Madlener, &. C. (1995) Virology 207, 460–466.
Durner, J., & Klessig, D. F. (1995) Proc. Natl. Acad. Sci. USA 92, 11312–11316.
Durner, J., & Klessig, D. F. (1996) J. Biol. Chem., 271, 28492–28501.
Jonak, C., Pay, A., Bogre, L., Hirt, H., & Heberle–Bors, E. (1993) Plant J. 3, 611–617.
Jonak, C., Kiegerl, S., Ligterink, W., Barker, P.J., Huskisson, N.S. & Hirt, L. (1996) Proc. Natl. Acad. Sci. USA 93, 11274–11279.
Klessig, D.F. & Malamy, J. (1994) Plant Mol. Biol. 26, 1439–1458.
Knetsch, M. L. W., Wang, M., Snaar–Jagalska, B. E., & Heimovaara–Dijkstra, S. (1996) Plant Cell 8, 1061–1067.
Levine, A., Tenhaken, R., Dixon, R., & Lamb, C. (1994) Cell 79, 583–593.
Mizoguchi, T., Hayashida, N., Yamaguchi–Shinozaki, K., Kamada, H., & Shinozaki, K. (1993) FEBS Lett. 336, 440–444.
Mizoguchi, T., Gotoh, Y., Nishida, E., Yamaguchi–Shinozaki, K., Hayashida, N., Iwasaki, T., Kamada, H., & Shinozaki, K. (1994) Plant J. 5, 111–122.
Mizoguchi, T., Irie, K., Hirayama, T., Hayashida, N., Yamaguchi–Shinozaki, K., Matsumota, K., & Shinozaki, K. (1996) Proc. Natl. Acad. Sci. USA 93, 765–769.
Nishihama, R., Banno, H., Shibata, W., Hirano, K., Nakashima, M., Usami, S. & Machida, Y. (1995) Plant Cell Physiol. 36, 749–757.
Ryals, J., Uknes, S., & Ward, E. (1994) Plant Physiol. 104, 1109–1112.
Seo, S., Okamoto, M., Seto, H., Ishizuka, K., Sano, H., & Ohashi, Y. (1995) Science 270, 1988–1992.
Suzuki, K. & Shinshi, H. (1995) Plant Cell 7, 639–647.
Usami, S., Banno, H., Ito, Y., Nishihama, R. & Machida, Y. (1995) Proc. Natl. Acad. Sci. USA 92, 8660–8664.
Wilson, C., Anglmayer, R., Vicente, O., and Haberle–Bors, E. (1995) Eur. J. Biochem. 233, 249–257.

*Primary Examiner*—Rebecca E. Prouty
*Attorney, Agent, or Firm*—Dann, Dorfman, Herrell and Skillman

[57] ABSTRACT

A salicylic acid-induced protein (SIP) kinase is disclosed. The kinase has a molecular weight of about 48 kDa and is activated in response to salicylic acid, $H_2O_2$ and infection with tobacco mosaic virus. The activation and enzymatic properties of the purified protein have been characterized. The partial amino acid sequence and complete nucleotide sequence of a cDNA encoding the SIP kinase demonstrate that it is a unique member of the mitogen-activated protein (MAP) kinase family. The novel SIP kinase may play a critical role in signal transduction for activation of plant defenses against microbial pathogens.

10 Claims, 16 Drawing Sheets

```
                                                    Peptide 1: NIFEVTAK
SIPK    (100%)  MDGSGQ-QTDTMMSDAGAEQPPTAPQPVAGMDNIPATLSHGGRFIQYNIFGNIFEVTAKYKPPIL
Ntf4    ( 93%)  ...PAH-....V....AGQ..APPS.....I........................M
Msk7    ( 89%)  .E.G.APPA..V....A------PAP.QM.IE....V....................M
WIPK    ( 73%)  MADANMGAGGGQFPDF.SV.T...QYV.FD....F...I.T..R...M
MMK4    ( 75%)  MARVNQN.VAEF..VQT...Q.V...V...L.......R...M
AtMPK3  ( 74%)  MNTGGGQYTDF..VDT...Q..S.D...SL..I.S..R...I
Ntf6    ( 66%)  MENETNEKLEIKGIPT.E.KYVE..VL..F....S..I...Q
Ntf3    ( 56%)  MATPVEPPNGIRTP.KHY--.SMWQSL..IDT..V.-.K SIPK    PIGKGAYGIVCSALNSETIENVAIKKIANAFDNKIDAKRTLREIKLLRHMDHENIVAIRDIIPPPQREAF
Ntf4    .................N.H...............................................
Msk7    ..............H....N.H..V....................V......V......V.
WIPK    ...R........V..T.LN.M..V........IYM..........L.....VIGL..V....L.RE.
MMK4    ...R.....:..L..T..N.L..V........HM...........L....VIGL..V....L.RE.
AtMPK3  ...R........V.DT..N.L..M........HM...........L.....I....VV...L.RQ.
Ntf6    .V.R.....M..C.T....K.E......G...E.R...........S......IK.K..VR..D..E.
Ntf3    ...R........SV.R..N.K.......N...E.R...L......LR...VI.LK.VMM.IH.RS.
                I            II              III                 IV Peptide 2: DLKPSNLLLNAN
SIPK    NDVYIAYELMDTDLHQIIRSNQGLSEEHCQYFLYQILRGLKYIHSANVLHRDLKPSNLLLNANCDLKICD
Ntf4    ....................................................-...............
Msk7    ...................A.................................................
WIPK    S.....T..............D.....M..L..............................V.........
MMK4    .....TT............N..D..............R......II......................I.
AtMPK3  S....ST...............S...........L..........II......................
Ntf6    .....V...........S.A.TDD........L......V..........................
Ntf3    K...LV...........K.S.T..ND......F.L.......L....I......G...I..........
             V                                          VI
                           *
        Peptide 3: WYRPPELLLN         Peptide 4: KPLFPGR
SIPK    FGLARVTSETD-FMTEYVVTRWYRPPELLLNSSDYTAAIDVWSVGCIFMELMDRKPLFPGRDHVHQLRLI
Ntf4    ...........-.........A..........................................L
Msk7    ...........-.........A..........................................L
WIPK    .....PNI.NE-N........A..................N....G.K.....I..L
MMK4    .....P.M.S.-.........A..........S.........NK.....K.....M..L
AtMPK3  .....P..N...-........A..................N....K.....M..L
Ntf6    .....T...A.-.........A......CTE......I......L...IK.E.......YAQ..G..
Ntf3    .....TS.GK.Q.........A.....CCDN.GTS.........A..LG...V...TECLN..K..
            VII         VIII          IX
                                                |
                    Peptide 5 & 6: AIDLVEKMLTFDPR
SIPK    MELIGTPSEAEMEFL-NENAKRYIRQLPLYRRQSFTEKFPHVHPTAIDLVEKMLTFDPRRRITVEGALAH
Ntf4    ...............-..................V.....N.A.................D....
Msk7    ........DDLG..-...........P......Q........E................K.....D....
WIPK    T..L...T..DLG..Q..D........QHP..QLA.V....N.L.....D......T......E..D.
MMK4    T..L...TD.DVGLVK.DD.R.......Q.P..PLNRV......L.....D......I..T......E....
AtMPK3  T..L...T.SDLG.TH..D........NFP..PLAKL.S..N.M.....DR......N.......Q..N.
Ntf6    IA.L.S.EDSDLG..RSD...RK.VKH..RVP.HP.SQ...D.S.L.L..A.R..V...AK.....D..N.
Ntf3    INIL.SQR.EDI..ID.PK.RK..KS..YSPGTP.SRLY..A..L....LQR..V...SK....S.IE..Q.
            X                                                      XI SIPK    PYLNSLHDISDEPICMTPFSFDFEQHALTEEQMKELIYRESLAFNPEYQHM
Ntf4    ...T......V.....N.....................G.........
Msk7    ...T......V..........................A.........Q
WIPK    ...AK...AG.....PV........QGIG...I.DM..Q.A.SL....A
MMK4    ...EK...VA.....E....E....QH.D...I..M....A..L....A
AtMPK3  Q..AK...PN.....QK....E....QP.D...I..M..Q.AI.L..T.G
Ntf6    .F.I...E.NE..V.DS..N.....AS.S.DDI....WN.A.K.D.NTMK
Ntf3    ..MSP.Y.PNTD.PAQV.INL.IDED-.G..TIR.MMWS.I.EYH..AATAAMEVVL
```

Figure 14

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
       (A) LENGTH: 1544 base pairs
       (B) TYPE: nucleic acid
       (C) STRANDEDNESS: both
       (D) TOPOLOGY: unknown (ii) MOLECULE TYPE: cDNA (iii) HYPOTHETICAL: NO (iv) ANTI-SENSE: NO (v) FRAGMENT TYPE:

(vi) ORIGINAL SOURCE: tobacco (xi) SEQUENCE DESCRIPTION: SEQ ID NO:1:

```
CACAATTCCA CATATTCATT GACATACTAC GGCCCTTCTT CCCTAATTTT AAGACAAAGG     60
AAAAAAAGTA ATTATTGATT CTTCTAGGAT TTACAATTTT TGTTGACGAA TTTTCCAAAA    120
AAAAAAATAT GGATGGTTCT GGTCAGCAGA CGGACACGAT GATGTCTGAT GCGGGGCGG     180
AGCAGCCACC TACGGCGCCG CAGCCGGTGG CCGGTATGGA TAATATTCCG GCGACGTTGA    240
GCCACGGTGG CAGGTTCATT CAATACAATA TATTTGGTAA TATATTTGAA GTTACTGCTA    300
AATATAAGCC TCCTATTTTG CCTATTGGTA AAGGTGCTTA CGGCATCGTT TGTTCTGCTT    360
TGAACTCGGA GACAATTGAG AACGTAGCGA TAAAGAAAAT CGCAAATGCT TTTGATAACA    420
AGATTGATGC CAAGAGGACT TGAGAGAGA TCAAGCTTCT TCGGCATATG GATCATGAAA     480
ACATTGTTGC GATCAGAGAT ATAATTCCAC CACCACAGAG AGAGGCCTTT AATGATGTTT    540
ATATTGCGTA TGAGCTTATG GATACTGATC TCCATCAAAT TATTCGCTCT AATCAGGGTT    600
TATCTGAGGA GCACTGTCAG TATTTCTTGT ATCAGATCCT CCGAGGGTTG AAATACATAC    660
ATTCTGCGAA TGTTCTGCAC AGGGACTTGA AGCCTAGCAA TCTCCTGTTG AATGCCAACT    720
GTGATTTAAA GATATGTGAT TTTGGGCTAG CTCGTGTCAC TTCTGAAACT GACTTTATGA    780
CGGAATATGT TGTGACAAGA TGGTATCGTC CACCTGAGCT GTTGTTAAAT TCGTCTGACT    840
ATACTGCAGC AATTGACGTA TGGTCAGTGG GTTGCATTTT CATGGAATTG ATGGACAGGA    900
AACCCCTATT TCCTGGTAGA GATCACGTAC ACCAGCTGCG TCTTATTATG GAGTTGATTG    960
GTACTCCTTC AGAGGCTGAA ATGGAGTTTT TAAATGAGAA TGCAAAACGA TACATCCGCC   1020
AACTTCCTCT TTACCGTCGA CAATCATTCA CTGAAAAGTT TCCACATGTA CACCCAACTG   1080
CAATTGATCT TGTCGAGAAA ATGCTGACAT TTGATCCTAG AAGGAGAATA ACAGTTGAAG   1140
GTGCACTTGC ACATCCTTAC CTGAACTCGC TCCACGATAT TAGTGACGAG CCCATTTGCA   1200
TGACTCCCTT TAGCTTCGAC TTTGAACAGC ATGCCCTTAC GGAGGAACAG ATGAAGGAGC   1260
TGATTTACAG GGAGTCGCTT GCATTTAATC CTGAATACCA GCATATGTGA ATAATTGCTG   1320
GTAAGATTGT TGTCAGTTTG ATCTCCAACT GACAATTTGT CCCTCCATGT ATATATGTGT   1380
GCACTTCGTC CGAAACACGG ATGGCTTTCT TATGCAAACA CTTAGTTATG AAGCTGATTT   1440
GTGTAAAGAA TTGTTTGATG TATCTGATGA GGTGGATCGC TTGTATTGGT TCTGTTTTAA   1500
TTTACTGAAG TCATAGTGGA CGAAAAAAAA AAAAAAAAA AAAA                     1544
```

(2) INFORMATION FOR SEQ ID NO:2:

(i) SEQUENCE CHARACTERISTICS:
        (A) LENGTH: 393 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (v) FRAGMENT TYPE: internal (vi) ORIGINAL SOURCE:

(xi) SEQUENCE DESCRIPTION: SEQ ID NO:2:

```
Met Asp Gly Ser Gly Gln Gln Thr Asp Thr Met Met Ser Asp Ala Gly
 1               5                  10                  15

Ala Glu Gln Pro Pro Thr Ala Pro Gln Pro Val Ala Gly Met Asp Asn
            20                  25                  30

Ile Pro Ala Thr Leu Ser His Gly Gly Arg Phe Ile Gln Tyr Asn Ile
        35                  40                  45

Phe Gly Asn Ile Phe Glu Val Thr Ala Lys Tyr Lys Pro Pro Ile Leu
50                  55                  60

Pro Ile Gly Lys Gly Ala Tyr Gly Ile Val Cys Ser Ala Leu Asn Ser
65                  70                  75                  80

Glu Thr Ile Glu Asn Val Ala Ile Lys Lys Ile Ala Asn Ala Phe Asp
                85                  90                  95

Asn Lys Ile Asp Ala Lys Arg Thr Leu Arg Glu Ile Lys Leu Leu Arg
            100                 105                 110

His Met Asp His Glu Asn Ile Val Ala Ile Arg Asp Ile Ile Pro Pro
        115                 120                 125

Pro Gln Arg Glu Ala Phe Asn Asp Val Tyr Ile Ala Tyr Glu Leu Met
    130                 135                 140

Asp Thr Asp Leu His Gln Ile Ile Arg Ser Asn Gln Gly Leu Ser Glu
145                 150                 155                 160

Glu His Cys Gln Tyr Phe Leu Tyr Gln Ile Leu Arg Gly Leu Lys Tyr
                165                 170                 175

Ile His Ser Ala Asn Val Leu His Arg Asp Leu Lys Pro Ser Asn Leu
            180                 185                 190 eu Leu Asn Ala Asn Cys Asp Leu Lys Ile Cys Asp Phe Gly Leu Ala
        195                 200                 205

Arg Val Thr Ser Glu Thr Asp Phe Met Thr Glu Tyr Val Val Thr Arg
    210                 215                 220

Trp Tyr Arg Pro Pro Glu Leu Leu Leu Asn Ser Ser Asp Tyr Thr Ala
225                 230                 235                 240

Ala Ile Asp Val Trp Ser Val Gly Cys Ile Phe Met Glu Leu Met Asp
                245                 250                 255

Arg Lys Pro Leu Phe Pro Gly Arg Asp His Val His Gln Leu Arg Leu
            260                 265                 270

Ile Met Glu Leu Ile Gly Thr Pro Ser Glu Ala Glu Met Glu Phe Leu
        275                 280                 285

Asn Glu Asn Ala Lys Arg Tyr Ile Arg Gln Leu Pro Leu Tyr Arg Arg
    290                 295                 300

Gln Ser Phe Thr Glu Lys Phe Pro His Val His Pro Thr Ala Ile Asp
305                 310                 315                 320
```

-continued

```
Leu Val Glu Lys Met Leu Thr Phe Asp Pro Arg Arg Ile Thr Val
                325                 330                 335

Glu Gly Ala Leu Ala His Pro Tyr Leu Asn Ser Leu His Asp Ile Ser
                340                 345                 350

Asp Glu Pro Ile Cys Met Thr Pro Phe Ser Phe Asp Phe Glu Gln His
                355                 360                 365

Ala Leu Thr Glu Glu Gln Met Lys Glu Leu Ile Tyr Arg Glu Ser Leu
     370                 375                 380

Ala Phe Asn Pro Glu Tyr Gln His Met
385                 390
```

(2) INFORMATION FOR SEQ ID NO:3:

(i) SEQUENCE CHARACTERISTICS:
        (A) LENGTH: 393 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:3:

```
Met Asp Gly Pro Ala His Gln Thr Asp Thr Val Met Ser Asp Ala Ala
 1               5                  10                  15

Gly Gln Gln Pro Ala Pro Pro Ser Gln Pro Val Ala Gly Ile Asp Asn
                20                  25                  30

Ile Pro Ala Thr Leu Ser His Gly Gly Arg Phe Ile Gln Tyr Asn Ile
                35                  40                  45

Phe Gly Asn Ile Phe Glu Val Thr Ala Lys Tyr Lys Pro Pro Ile Met
     50                  55                  60

Pro Ile Gly Lys Gly Ala Tyr Gly Ile Val Cys Ser Ala Leu Asn Ser
65                   70                  75                  80

Glu Thr Asn Glu His Val Ala Ile Lys Lys Ile Ala Asn Ala Phe Asp
                85                  90                  95

Asn Lys Ile Asp Ala Lys Arg Thr Leu Arg Glu Ile Lys Leu Leu Arg
                100                 105                 110

His Met Asp His Glu Asn Ile Val Ala Ile Arg Asp Ile Ile Pro Pro
                115                 120                 125

Pro Gln Arg Glu Ala Phe Asn Asp Val Tyr Ile Ala Tyr Glu Leu Met
     130                 135                 140

Asp Thr Asp Leu His Gln Ile Ile Arg Ser Asn Gln Gly Leu Ser Glu
145                 150                 155                 160

Glu His Cys Gln Tyr Phe Leu Tyr Gln Ile Leu Arg Gly Leu Lys Tyr
                165                 170                 175

Ile His Ser Ala Asn Val Leu His Arg Asp Leu Lys Pro Ser Asn Leu
                180                 185                 190

Leu Leu Asn Ala Asn Cys Asp Leu Lys Ile Cys Asp Phe Gly Leu Ala
                195                 200                 205

Arg Val Thr Ser Glu Thr Asp Phe Met Thr Glu Tyr Val Val Thr Arg
     210                 215                 220

Trp Tyr Arg Ala Pro Glu Leu Leu Leu Asn Ser Ser Asp Tyr Thr Ala
```

```
                225                 230                 235                 240
Ala Ile Asp Val Trp Ser Val Gly Cys Ile Phe Met Glu Leu Met Asp
                    245                 250                 255
Arg Lys Pro Leu Phe Pro Gly Arg Asp His Val His Gln Leu Arg Leu
            260                 265                 270
Leu Met Glu Leu Ile Gly Thr Pro Ser Glu Ala Glu Met Glu Phe Leu
        275                 280                 285
Asn Glu Asn Ala Lys Arg Tyr Ile Arg Gln Leu Pro Leu Tyr Arg Arg
    290                 295                 300
Gln Ser Phe Val Glu Lys Phe Pro His Val Asn Pro Ala Ala Ile Asp
305                 310                 315                 320
Leu Val Glu Lys Met Leu Thr Phe Asp Pro Arg Arg Arg Ile Thr Val
                325                 330                 335
Glu Asp Ala Leu Ala His Pro Tyr Leu Thr Ser Leu His Asp Ile Ser
                340                 345                 350
Asp Glu Pro Val Cys Met Thr Pro Phe Asn Phe Asp Phe Glu Gln His
            355                 360                 365
Ala Leu Thr Glu Glu Gln Met Lys Glu Leu Ile Tyr Arg Glu Gly Leu
        370                 375                 380
Ala Phe Asn Pro Glu Tyr Gln His Met
385                 390

(2) INFORMATION FOR SEQ ID NO:4:

(i) SEQUENCE CHARACTERISTICS:
        (A) LENGTH: 387 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:4:

Met Glu Gly Gly Gly Ala Pro Pro Ala Asp Thr Val Met Ser Asp Ala
1               5                   10                  15
Ala Pro Ala Pro Pro Gln Met Gly Ile Glu Asn Ile Pro Ala Val Leu
            20                  25                  30
Ser His Gly Gly Arg Phe Ile Gln Tyr Asn Ile Phe Gly Asn Ile Phe
        35                  40                  45
Glu Val Thr Ala Lys Tyr Lys Pro Pro Ile Met Pro Ile Gly Lys Gly
    50                  55                  60
Ala Tyr Gly Ile Val Cys Ser Ala His Asn Ser Glu Thr Asn Glu His
65                  70                  75                  80
Val Ala Val Lys Lys Ile Ala Asn Ala Phe Asp Asn Lys Ile Asp Ala
                85                  90                  95
Lys Arg Thr Leu Arg Glu Ile Lys Leu Leu Arg His Met Asp His Glu
            100                 105                 110
Asn Val Val Ala Ile Arg Asp Ile Val Pro Pro Pro Gln Arg Glu Val
        115                 120                 125
Phe Asn Asp Val Tyr Ile Ala Tyr Glu Leu Met Asp Thr Asp Leu His
    130                 135                 140
```

```
Gln Ile Ile Arg Ser Asn Gln Ala Leu Ser Glu Glu His Cys Gln Tyr
145                 150                 155                 160

Phe Leu Tyr Gln Ile Leu Arg Gly Leu Lys Tyr Ile His Ser Ala Asn
            165                 170                 175

Val Leu His Arg Asp Leu Lys Pro Ser Asn Leu Leu Leu Asn Ala Asn
            180                 185                 190

Cys Asp Leu Lys Ile Cys Asp Phe Gly Leu Ala Arg Val Thr Ser Glu
            195                 200                 205

Thr Asp Phe Met Thr Glu Tyr Val Val Thr Arg Trp Tyr Arg Ala Pro
210                 215                 220

Glu Leu Leu Leu Asn Ser Ser Asp Tyr Thr Ala Ala Ile Asp Val Trp
225                 230                 235                 240

Ser Val Gly Cys Ile Phe Met Glu Leu Met Asp Arg Lys Pro Leu Phe
            245                 250                 255

Pro Gly Arg Asp His Val His Gln Leu Arg Leu Leu Met Glu Leu Ile
            260                 265                 270

Gly Thr Pro Ser Glu Asp Asp Leu Gly Phe Leu Asn Glu Asn Ala Lys
            275                 280                 285

Arg Tyr Ile Arg Gln Leu Pro Pro Tyr Arg Arg Gln Ser Phe Gln Glu
290                 295                 300

Lys Phe Pro His Val His Pro Glu Ala Ile Asp Leu Val Glu Lys Met
305                 310                 315                 320

Leu Thr Phe Asp Pro Arg Lys Arg Ile Thr Val Glu Asp Ala Leu Ala
            325                 330                 335

His Pro Tyr Leu Thr Ser Leu His Asp Ile Ser Asp Glu Pro Val Cys
            340                 345                 350

Met Thr Pro Phe Ser Phe Asp Phe Glu Gln His Ala Leu Thr Glu Glu
            355                 360                 365

Gln Met Lys Glu Leu Ile Tyr Arg Glu Ala Leu Ala Phe Asn Pro Glu
370                 375                 380

Tyr Gln Gln
385

(2) INFORMATION FOR SEQ ID NO:5:

(i) SEQUENCE CHARACTERISTICS:
        (A) LENGTH: 375 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:5:

Met Ala Asp Ala Asn Met Gly Ala Gly Gly Gln Phe Pro Asp Phe
1               5                   10                  15

Pro Ser Val Leu Thr His Gly Gly Gln Tyr Val Gln Phe Asp Ile Phe
            20                  25                  30

Gly Asn Phe Phe Glu Ile Thr Thr Lys Tyr Arg Pro Pro Ile Met Pro
            35                  40                  45

Ile Gly Arg Gly Ala Tyr Gly Ile Val Cys Ser Val Leu Asn Thr Glu
50                  55                  60
```

Leu Asn Glu Met Val Ala Val Lys Lys Ile Ala Asn Ala Phe Asp Ile
 65                  70                  75                  80

Tyr Met Asp Ala Lys Arg Thr Leu Arg Glu Ile Lys Leu Leu Arg His
                 85                  90                  95

Leu Asp His Glu Asn Val Ile Gly Leu Arg Asp Val Ile Pro Pro Pro
                100                 105                 110

Leu Arg Arg Glu Phe Ser Asp Val Tyr Ile Ala Thr Glu Leu Met Asp
                115                 120                 125

Thr Asp Leu His Gln Ile Ile Arg Ser Asn Gln Gly Leu Ser Glu Asp
            130                 135                 140

His Cys Gln Tyr Phe Met Tyr Gln Leu Leu Arg Gly Leu Lys Tyr Ile
            145                 150                 155                 160

His Ser Ala Asn Val Leu His Arg Asp Leu Lys Pro Ser Asn Leu Leu
                165                 170                 175

Val Asn Ala Asn Cys Asp Leu Lys Ile Cys Asp Phe Gly Leu Ala Arg
                180                 185                 190

Pro Asn Ile Glu Asn Glu Asn Met Thr Glu Tyr Val Val Thr Arg Trp
                195                 200                 205

Tyr Arg Ala Pro Glu Leu Leu Leu Asn Ser Ser Asp Tyr Thr Ala Ala
            210                 215                 220

Ile Asp Val Trp Ser Val Gly Cys Ile Phe Met Glu Leu Met Asn Arg
225                 230                 235                 240

Lys Pro Leu Phe Gly Gly Lys Asp His Val His Gln Ile Arg Leu Leu
                245                 250                 255

Thr Glu Leu Leu Gly Thr Pro Thr Glu Ala Asp Leu Gly Phe Leu Gln
                260                 265                 270

Asn Glu Asp Ala Lys Arg Tyr Ile Arg Gln Leu Pro Gln His Pro Arg
            275                 280                 285

Gln Gln Leu Ala Glu Val Phe Pro His Val Asn Pro Leu Ala Ile Asp
            290                 295                 300

Leu Val Asp Lys Met Leu Thr Phe Asp Pro Thr Arg Arg Ile Thr Val
305                 310                 315                 320

Glu Glu Ala Leu Asp His Pro Tyr Leu Ala Lys Leu His Asp Ala Gly
                325                 330                 335

Asp Glu Pro Ile Cys Pro Val Pro Phe Ser Phe Asp Phe Glu Gln Gln
                340                 345                 350

Gly Ile Gly Glu Glu Gln Ile Lys Asp Met Ile Tyr Gln Glu Ala Leu
            355                 360                 365

Ser Leu Asn Pro Glu Tyr Ala
370                 375

(2) INFORMATION FOR SEQ ID NO:6:

(i) SEQUENCE CHARACTERISTICS:
        (A) LENGTH: 371 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:6:

```
Met Ala Arg Val Asn Gln Asn Gly Val Ala Glu Phe Pro Ala Val Gln
  1               5                  10                  15

Thr His Gly Gly Gln Phe Val Gln Tyr Asn Val Phe Gly Asn Leu Phe
                 20                  25                  30

Glu Val Thr Ala Lys Tyr Arg Pro Pro Ile Met Pro Ile Gly Arg Gly
             35                  40                  45

Ala Tyr Gly Ile Val Cys Ser Leu Leu Asn Thr Glu Thr Asn Glu Leu
 50                  55                  60

Val Ala Val Lys Lys Ile Ala Asn Ala Phe Asp Asn His Met Asp Ala
 65                  70                  75                  80

Lys Arg Thr Leu Arg Glu Ile Lys Leu Leu Arg His Leu Asp His Glu
                 85                  90                  95

Asn Val Ile Gly Leu Arg Asp Val Ile Pro Pro Leu Arg Arg Glu
                100                 105                 110

Phe Asn Asp Val Tyr Ile Thr Thr Glu Leu Met Asp Thr Asp Leu His
                115                 120                 125

Gln Ile Ile Arg Ser Asn Gln Asn Leu Ser Asp Glu His Cys Gln Tyr
130                 135                 140

Phe Leu Tyr Gln Ile Leu Arg Gly Leu Arg Tyr Ile His Ser Ala Asn
145                 150                 155                 160

Ile Ile His Arg Asp Leu Lys Pro Ser Asn Leu Leu Leu Asn Ala Asn
                165                 170                 175

Cys Asp Leu Lys Ile Ile Asp Phe Gly Leu Ala Arg Pro Thr Met Glu
                180                 185                 190

Ser Asp Phe Met Thr Glu Tyr Val Val Thr Arg Trp Tyr Arg Ala Pro
                195                 200                 205

Glu Leu Leu Leu Asn Ser Ser Asp Tyr Thr Ser Ala Ile Asp Val Trp
210                 215                 220

Ser Val Gly Cys Ile Phe Met Glu Leu Met Asn Lys Lys Pro Leu Phe
225                 230                 235                 240

Pro Gly Lys Asp His Val His Gln Met Arg Leu Leu Thr Glu Leu Leu
                245                 250                 255

Gly Thr Pro Thr Asp Ala Asp Val Gly Leu Val Lys Asn Asp Asp Ala
                260                 265                 270

Arg Arg Tyr Ile Arg Gln Leu Pro Gln Tyr Pro Arg Gln Pro Leu Asn
                275                 280                 285

Arg Val Phe Pro His Val His Pro Leu Ala Ile Asp Leu Val Asp Lys
                290                 295                 300

Met Leu Thr Ile Asp Pro Thr Arg Arg Ile Thr Val Glu Glu Ala Leu
305                 310                 315                 320

Ala His Pro Tyr Leu Glu Lys Leu His Asp Val Ala Asp Glu Pro Ile
                325                 330                 335

Cys Met Glu Pro Phe Ser Phe Glu Phe Glu Gln Gln His Leu Asp Glu
                340                 345                 350

Glu Gln Ile Lys Glu Met Ile Tyr Arg Glu Ala Leu Ala Leu Asn Pro
                355                 360                 365

Glu Tyr Ala
370
```

(2) INFORMATION FOR SEQ ID NO:7:

(i) SEQUENCE CHARACTERISTICS:
      (A) LENGTH: 370 amino acids
      (B) TYPE: amino acid (C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:7:

```
Met Asn Thr Gly Gly Gly Gln Tyr Thr Asp Phe Pro Ala Val Asp Thr
  1               5                  10                  15

His Gly Gly Gln Phe Ile Ser Tyr Asp Ile Phe Gly Ser Leu Phe Glu
             20                  25                  30

Ile Thr Ser Lys Tyr Arg Pro Pro Ile Ile Pro Ile Gly Arg Gly Ala
             35                  40                  45

Tyr Gly Ile Val Cys Ser Val Leu Asp Thr Glu Thr Asn Glu Leu Val
 50                  55                  60

Ala Met Lys Lys Ile Ala Asn Ala Phe Asp Asn His Met Asp Ala Lys
 65                  70                  75                  80

Arg Thr Leu Arg Glu Ile Lys Leu Leu Arg His Leu Asp His Glu Asn
             85                  90                  95

Ile Ile Ala Ile Arg Asp Val Val Pro Pro Pro Leu Arg Arg Gln Phe
            100                 105                 110

Ser Asp Val Tyr Ile Ser Thr Glu Leu Met Asp Thr Asp Leu His Gln
            115                 120                 125

Ile Ile Arg Ser Asn Gln Ser Leu Ser Glu Glu His Cys Gln Tyr Phe
130                 135                 140

Leu Tyr Gln Leu Leu Arg Gly Leu Lys Tyr Ile His Ser Ala Asn Ile
145                 150                 155                 160

Ile His Arg Asp Leu Lys Pro Ser Asn Leu Leu Asn Ala Asn Cys
            165                 170                 175

Asp Leu Lys Ile Cys Asp Phe Gly Leu Ala Arg Pro Thr Ser Glu Asn
            180                 185                 190

Asp Phe Met Thr Glu Tyr Val Val Thr Arg Trp Tyr Arg Ala Pro Glu
            195                 200                 205

Leu Leu Leu Asn Ser Ser Asp Tyr Thr Ala Ala Ile Asp Val Trp Ser
210                 215                 220

Val Gly Cys Ile Phe Met Glu Leu Met Asn Arg Lys Pro Leu Phe Pro
225                 230                 235                 240

Gly Lys Asp His Val His Gln Met Arg Leu Leu Thr Glu Leu Leu Gly
            245                 250                 255

Thr Pro Thr Glu Ser Asp Leu Gly Phe Thr His Asn Glu Asp Ala Lys
            260                 265                 270

Arg Tyr Ile Arg Gln Leu Pro Asn Phe Pro Arg Gln Pro Leu Ala Lys
            275                 280                 285

Leu Phe Ser His Val Asn Pro Met Ala Ile Asp Leu Val Asp Arg Met
            290                 295                 300

Leu Thr Phe Asp Pro Asn Arg Arg Ile Thr Val Glu Gln Ala Leu Asn
305                 310                 315                 320

His Gln Tyr Leu Ala Lys Leu His Asp Pro Asn Asp Glu Pro Ile Cys
            325                 330                 335

Gln Lys Pro Phe Ser Phe Glu Phe Glu Gln Pro Leu Asp Glu Glu
            340                 345                 350
```

-continued

```
Gln Ile Lys Glu Met Ile Tyr Gln Glu Ala Ile Ala Leu Asn Pro Thr
            355                 360                 365
Tyr Gly
    370
```

(2) INFORMATION FOR SEQ ID NO:8:

(i) SEQUENCE CHARACTERISTICS:
        (A) LENGTH: 371 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:8:

```
Met Glu Asn Glu Thr Asn Glu Lys Leu Glu Ile Lys Gly Ile Pro Thr
  1               5                  10                  15

His Glu Gly Lys Tyr Val Glu Tyr Asn Val Leu Gly Asn Phe Phe Glu
                 20                  25                  30

Val Thr Ser Lys Tyr Ile Pro Pro Ile Gln Pro Val Gly Arg Gly Ala
             35                  40                  45

Tyr Gly Met Val Cys Cys Ala Thr Asn Ser Glu Thr Lys Glu Glu Val
         50                  55                  60

Ala Ile Lys Lys Ile Gly Asn Ala Phe Glu Asn Arg Ile Asp Ala Lys
 65                  70                  75                  80

Arg Thr Leu Arg Glu Ile Lys Leu Leu Ser His Met Asp His Glu Asn
                 85                  90                  95

Ile Ile Lys Ile Lys Asp Ile Val Arg Pro Pro Asp Arg Glu Glu Phe
                100                 105                 110

Asn Asp Val Tyr Ile Val Tyr Glu Leu Met Asp Thr Asp Leu His Gln
            115                 120                 125

Ile Ile Arg Ser Ser Gln Ala Leu Thr Asp Asp His Cys Gln Tyr Phe
        130                 135                 140

Leu Tyr Gln Leu Leu Arg Gly Leu Lys Tyr Val His Ser Ala Asn Val
145                 150                 155                 160

Leu His Arg Asp Leu Lys Pro Ser Asn Leu Leu Asn Ala Asn Cys
                165                 170                 175

Asp Leu Lys Ile Cys Asp Phe Gly Leu Ala Arg Thr Thr Ser Glu Ala
            180                 185                 190

Asp Phe Met Thr Glu Tyr Val Val Thr Arg Trp Tyr Arg Ala Pro Glu
        195                 200                 205

Leu Leu Leu Asn Cys Thr Glu Tyr Thr Ala Ala Ile Asp Ile Trp Ser
    210                 215                 220

Val Gly Cys Ile Leu Met Glu Leu Ile Lys Arg Glu Pro Leu Phe Pro
225                 230                 235                 240

Gly Arg Asp Tyr Ala Gln Gln Leu Gly Leu Ile Ile Ala Leu Leu Gly
                245                 250                 255

Ser Pro Glu Asp Ser Asp Leu Gly Phe Leu Arg Ser Asp Asn Ala Arg
            260                 265                 270

Lys Tyr Val Lys His Leu Pro Arg Val Pro Arg His Pro Phe Ser Gln
```

```
                    275                 280                 285
Lys Phe Pro Asp Val Ser Pro Leu Ala Leu Asp Leu Ala Glu Arg Met
    290                 295                 300

Leu Val Phe Asp Pro Ala Lys Arg Ile Thr Val Glu Asp Ala Leu Asn
305                 310                 315                 320

His Pro Phe Leu Ile Ser Leu His Glu Ile Asn Glu Glu Pro Val Cys
                325                 330                 335

Asp Ser Pro Phe Asn Phe Asp Phe Glu Gln Ala Ser Leu Ser Glu Asp
            340                 345                 350

Asp Ile Lys Glu Leu Ile Trp Asn Glu Ala Leu Lys Phe Asp Pro Asn
        355                 360                 365

Thr Met Lys
    370

(2) INFORMATION FOR SEQ ID NO:9:

(i) SEQUENCE CHARACTERISTICS:
        (A) LENGTH: 372 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:9:

Met Ala Thr Pro Val Glu Pro Pro Asn Gly Ile Arg Thr Pro Gly Lys
1               5                   10                  15

His Tyr Tyr Ser Met Trp Gln Ser Leu Phe Glu Ile Asp Thr Lys Tyr
            20                  25                  30

Val Pro Ile Lys Pro Ile Gly Arg Gly Ala Tyr Gly Ile Val Cys Ser
        35                  40                  45

Ser Val Asn Arg Glu Thr Asn Glu Lys Val Ala Ile Lys Lys Ile Asn
50                  55                  60

Asn Ala Phe Glu Asn Arg Ile Asp Ala Leu Arg Thr Leu Arg Glu Leu
65                  70                  75                  80

Lys Leu Leu Arg His Leu Arg His Glu Asn Val Ile Ala Leu Lys Asp
                85                  90                  95

Val Met Met Pro Ile His Arg Arg Ser Phe Lys Asp Val Tyr Leu Val
            100                 105                 110

Tyr Glu Leu Met Asp Thr Asp Leu His Gln Ile Ile Lys Ser Ser Gln
        115                 120                 125

Thr Leu Ser Asn Asp His Cys Gln Tyr Phe Leu Phe Gln Leu Leu Arg
    130                 135                 140

Gly Leu Lys Tyr Leu His Ser Ala Asn Ile Leu His Arg Asp Leu Lys
145                 150                 155                 160

Pro Gly Asn Leu Leu Ile Asn Ala Asn Cys Asp Leu Lys Ile Cys Asp
                165                 170                 175

Phe Gly Leu Ala Arg Thr Ser Ser Gly Lys Asp Gln Phe Met Thr Glu
            180                 185                 190

Tyr Val Val Thr Arg Trp Tyr Arg Ala Pro Glu Leu Leu Leu Cys Cys
        195                 200                 205
```

Asp Asn Tyr Gly Thr Ser Ile Asp Val Trp Ser Val Gly Cys Ile Phe
    210                 215                 220
Ala Glu Leu Leu Gly Arg Lys Pro Val Phe Pro Gly Thr Glu Cys Leu
225                 230                 235                 240
Asn Gln Leu Lys Leu Ile Ile Asn Ile Leu Gly Ser Gln Arg Glu Glu
                245                 250                 255
Asp Ile Glu Phe Ile Asp Asn Pro Lys Ala Arg Lys Tyr Ile Lys Ser
                260                 265                 270
Leu Pro Tyr Ser Pro Gly Thr Pro Phe Ser Arg Leu Tyr Pro His Ala
            275                 280                 285
His Pro Leu Ala Ile Asp Leu Leu Gln Arg Met Leu Val Phe Asp Pro
    290                 295                 300
Ser Lys Arg Ile Ser Val Ile Glu Ala Leu Gln His Pro Tyr Met Ser
305                 310                 315                 320
Pro Leu Tyr Asp Pro Asn Thr Asp Pro Pro Ala Gln Val Pro Ile Asn
                325                 330                 335
Leu Asp Ile Asp Glu Asp Leu Gly Glu Glu Thr Ile Arg Glu Met Met
            340                 345                 350
Trp Ser Glu Ile Leu Glu Tyr His Pro Glu Ala Ala Thr Ala Ala Met
        355                 360                 365
Glu Val Val Leu
    370

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:10:

Asn Ile Phe Glu Val Thr Ala Lys
1               5

(2) INFORMATION FOR SEQ ID NO:11:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:11:

Asp Leu Lys Pro Ser Asn Leu Leu Leu Asn Ala Asn
1               5                   10

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:12:

Trp Tyr Arg Pro Pro Glu Leu Leu Leu Asn
 1               5                   10

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:13:

Lys Pro Leu Phe Pro Gly Arg
 1               5

(2) INFORMATION FOR SEQ ID NO:14:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:14:

Ala Ile Asp Leu Val Glu Lys Met Leu Thr Phe Asp Pro Arg
 1               5                   10

SALICYLIC ACID INDUCED MAP KINASE AND ITS USE FOR ENHANCED DISEASE RESISTANCE IN PLANTS

This application claims priority to U.S. Provisional Application Ser. No. 60/029,805, filed Oct. 25, 1996, which is incorporated by reference herein.

Pursuant to 35 U.S.C. §202(c), it is acknowledged that the U.S. Government has certain rights in the invention described herein, which was made in part with funds from the National Science Foundation, Grant Number, MCB-9310371.

FIELD OF THE INVENTION

This invention relates to the fields of molecular biology and genetic transformation in higher plants. More specifically, the invention relates to novel genes and their encoded proteins that participate in the enhanced disease resistance pathway in multicellular plants.

BACKGROUND OF THE INVENTION

Several publications are referenced in this application in parentheses in order to more fully describe the state of the art to which this invention pertains. Full citations for these references are found at the end of the specification. The disclosure of each of these publications is incorporated by reference herein.

Activation of tobacco defense responses by tobacco mosaic virus (TMV) infection includes both local resistance, manifested as necrotic lesion formation resulting from host cell death at the site of infection (hypersensitive response, HR), and systemic resistance induced in the surrounding and distal uninfected parts of the plant (systemic acquired resistance, SAR) (Ryals et al., 1994; Dempsey and Klessig, 1995). Numerous studies have demonstrated that salicylic acid (SA) is an endogenous signal for the activation of several plant defense responses including synthesis of pathogenesis-related (PR) proteins (Ryals et al., 1994, Dempsey and Klessig, 1995). However, the components which transduce the signal between SA and PR genes remain to be elucidated.

Protein kinases and phosphatases play pivotal roles in regulating and coordinating many signal transduction pathways in living organisms, including but not limited to, cell division, cell differentiation, and responses to environmental stimuli (Hunter, 1995). In plants, protein phosphorylation has been implicated in responses to many signals, such as light, hormones, pathogen attack, temperature stress, and nutrient starvation (Stone and Walker, 1995). Several genes which encode putative protein kinases, including CTR1 (Kieber et al., 1993), ETR1 (Chang et al., 1993) and Pto (Martin et al., 1993) appear to participate in the transmission of signals generated by extracellular stimuli. The CTR1 and ETR1 protein kinases of Arabidopsis thaliana play a role in the ethylene signaling pathway. CTR1 is homologous to the mammalian Raf protein kinase which participates in the mitogen-activated protein (MAP) kinase cascade (Kieber et al., 1993). The Pto protein kinase from tomato, as well as its downstream kinase Pti1 which is phosphorylated by Pto, participate in conferring resistance to the pathogenic bacterium Pseudomonas syringae (Martin et al., 1993; Zhou et al., 1995).

The MAP kinase cascade is a major signaling system by which cells transduce extracellular stimuli into intracellular responses (Herskowitz 1995; Seger and Krebs, 1995; Votjek and Cooper, 1995; Kyriakis and Avruch, 1996). Extracellular signal-regulated protein kinases (ERKs) 1 and 2 were the first of the MAP kinase family to be cloned; they are activated by diverse extracellular stimuli. Other related mammalian MAP kinases include Jun N-terminal kinase/stress-activated protein kinases (JNK/SAPK) and p38 kinases (Seger and Krebs, 1995). MAP kinases are activated by phosphorylation on both threonine (T) and tyrosine (Y) residues within a TXY phosphorylation motif, where X can be Glu (E), Pro (P), or Gly (G). Three subfamilies of MAP kinases have been defined based on their phosphorylation motifs TEY, TPY, and TGY, which correspond to ERK1/2, JNK/SAPK, and p38 subfamilies, respectively (Kyriakis and Avruch, 1996).

The MAP kinase family is present in a diverse array of organisms including mammals, Xenopus, Drosophila, yeast, Dictyostelium, and plants. An increasing body of evidence suggests that MAP kinases play important roles in plants (Nishihama, et al., 1995). Seven MAP kinases have been identified in Arabidopsis. AtMPK1 and AtMPK2 are thought to be involved in cell proliferation (Mizoguchi, et al., 1993; Mizoguchi, et al., 1994), while AtMPK3 appears to play a role in responding to touch, cold and salinity stress (Mizoguchi et al., 1996). Several kinases upstream of the MAP kinase in the cascade have also been identified including cATMEKK1 from Arabidopsis and NPK1 from tobacco (Nishihama, et al., 1995; Mizoguchi, et al., 1996).

Several kinase activities, believed to be MAP kinases based on the fact that they preferentially phosphorylate myelin basic protein (MBP) and are themselves phosphorylated on tyrosine residues, have been shown to be activated by stress or phytohormones. These include the cutting (wounding)-induced p46 kinase (Usami et al., 1995; Seo et al., 1995), the fungal elicitor-induced p47 kinase from tobacco (Suzuki et al., 1995), and the abscisic acid-induced kinase from barley (Knetsch et al., 1996).

Protein phosphorylation/dephosphorylation events have been correlated with the activation of defense responses in a number of plants (Dietrich et al., 1990; Felix et al., 1991; Viard et al., 1994; Conrath et al., 1997). More recently, it has been shown that the activation of the potato PR-10a gene requires the phosphorylation of the nuclear factor PBF-1 (Despros et al., 1994). In addition, protein kinase inhibitors were able to block both the fungal elicitor-induced oxidative burst and the $H_2O_2$-mediated activation of defense genes in soybean suspension cells (Levine et al., 1994). Kinase(s) and/or phosphatase(s) also appear to regulate the activation of defense responses in tobacco, since lesion formation after TMV infection was inhibited by the phosphatase inhibitor okadaic acid (Dunigan et al., 1995). Okadaic acid also blocked the SA-mediated induction of PR-1 gene expression (Conrath et al., 1997). The kinase(s) and/or phosphatase(s) involved in these processes, however, remain to be identified.

It has been shown that the MAP kinases associated with several different signaling pathways are activated by $H_2O_2$ or other oxidative stresses in mammalian systems. These include JNK, ERK2, and the big mitogen-activated protein kinase 1 (BMK1; Abe et al., 1996; Lo et al., 1996; Guyton et al., 1996; Sundaresan et al., 1995). Thus, $H_2O_2$ appears to regulate a wide variety of different processes. In neutrophils, reactive oxygen species produced by the NADPH oxidase induce tyrosine phosphorylation, in addition to their role in bacterial killing (Fialko et al., 1994; Brumell et al., 1996). The prominent 42–44 kDa tyrosine-phosphorylated polypeptide induced by $H_2O_2$ was later shown to be MAP kinase that is phosphorylated on both tyrosine and threonine by a redox-sensitive MAP kinase kinase (MEK; Fialkow et al., 1994). In plants, $H_2O_2$ has been implicated in both the action of SA (Chen et al., 1993) and the induction of defense responses after pathogen invasion, exposure to ozone or UV light (Medhy, 1994; Levine et al., 1994; Kangasjarvi et al., 1994; Green and Fluhr, 1995).

SUMMARY OF THE INVENTION

A new member of the mitogen-activated protein (MAP) kinase family of enzymes has been discovered in accordance with the present invention. Referred to herein as salicylic acid-induced protein (SIP) kinase, the enzyme is structurally distinct from other MAP kinases. Another unique feature of SIP kinase is that it is activated by microbial pathogens, as well as by secondary plant defense signaling molecules, as described in greater detail below.

According to one aspect of the invention, an isolated MAP kinase protein of the invention is provided, which is activated by an agent that induces a disease defense response in plants. The protein comprises certain structural features such as (1) kinase subdomains I through XI of serine/threonine kinases, the (2) an N-terminal amino acid sequence which is residues 1–24 of Sequence I.D. No. 2 herein; and (3) sequence I.D. No. 12 within serine/threonine kinase subdomain VIII. In a preferred embodiment, the protein possesses an amino acid sequence greater than 93% homologous to Sequence I.D. No. 2, and most preferably possesses Sequence I.D. No. 2.

For purposes of this invention, a "disease defense response" means an change in metabolism, biosynthetic activity or gene expression that enhances the plant's ability to suppress the replication and spread of a microbial pathogen (i.e., to resist the microbial pathogen). Plants exhibit disease defense responses by way of several signal transduction pathways, as described in greater detail herein. Some of these pathways are at least partially dependent on salicylic acid as a secondary defense signaling molecule.

In another aspect of the invention, an isolated MAP kinase protein is provided which is activated by an agent that induces a disease defense response in plants by way of a signal transduction pathway that is at least partially dependent on salicylic acid as the secondary signaling defense molecule. Preferably, the protein is produced by a method comprising (1) exposing plant cells to an amount of salicylic acid effective to activate the protein to exhibit its kinase activity, (2) identifying the protein exhibiting the kinase activity, and (3) isolating the protein from the plant cells.

According to another aspect of the invention, an isolated protein having Sequence I.D. No. 2 is provided.

According to another aspect of the invention, there is provided a polypeptide produced by expression of an isolated nucleic acid sequence selected from: (a) Sequence I.D. No. 1; (b) an allelic variant of Sequence I.D. No. 1; (c) a natural mutant of Sequence I.D. No. 1; (d) a sequence hybridizing with part or all of a sequence complementary to Sequence I.D. No. 1 and encoding a polypeptide substantially the same as part or all of a polypeptide encoded by sequence I.D. No. 1; and (e) a sequence encoding part or all of a polypeptide having amino acid sequence I.D. No. 2.

According to another aspect of the invention, antibodies are provided that are immunologically specific for part or all of the proteins of the invention.

In yet another aspect of the present invention, an isolated nucleic acid molecule is provided, which includes an open reading frame encoding a MAP kinase protein that comprises kinase subdomains I through XI of serine/threonine kinases, the protein having an N-terminal amino acid sequence which is residues 1–24 of Sequence I.D. No. 2 herein and further comprising sequence I.D. No. 12 within serine/threonine kinase subdomain VIII, the protein also being activated by an agent that induces a disease defense response in plants. The nucleic acid molecule may be genomic DNA, cDNA or RNA. The open reading frame preferably encodes a protein having greater than 93% sequence homology with sequence I.D. No. 2.

According to yet another aspect of the invention, an isolated nucleic acid molecule is provided, which has a sequence selected from: (a) Sequence I.D. No. 1; (b) an allelic variant of Sequence I.D. No. 1; (c) a natural mutant of Sequence I.D. No. 1; (d) a sequence hybridizing with part or all of a sequence complementary to Sequence I.D. No. 1 and encoding a polypeptide substantially the same as part or all of a polypeptide encoded by sequence I.D. No. 1; and (e) a sequence encoding part or all of a polypeptide having amino acid sequence I.D. No. 2.

Also provided in accordance with the invention are oligonucleotides that specifically hybridize with the nucleic acid sequences set forth above, and recombinant DNA molecules comprising the nucleic acid molecules set forth above, operably linked to a vector.

According to yet another aspect of the invention, plant cells transformed with the aforementioned recombinant DNA molecules are provided. Transgenic plants comprising those recombinant DNA molecules are also provided.

The new MAP kinase described in greater detail below may play a key role in signal transduction for activation of plant defenses against microbial pathogens. Accordingly, the novel nucleic acid molecules, proteins, antibodies, plant cells and plants of the invention offer a significant advance in the field of plant molecular biology, as it pertains to enhancing the plant disease resistance response.

BRIEF DESCRIPTION OF THE DRAWINGS

In FIG. 1C, the same extracts from SA- or water-treated cells were tested using casein as a substrate. Only the results from SA-treated cells are shown. The position of the p48 SIP kinase is indicated by an asterisk (*). Molecular mass markers at left are given in kDa. In FIG. 1D, the p48 SIP kinase activities (●, SA-treated; ○, water-treated) were quantitated using a phosphoimager and the relative activities were plotted against time. Kinase activities were normalized to the level present at the zero time point, which was assigned a value of 1. In FIG. 1E, the dose response of p48 SIP kinase activation in tobacco suspension cells was plotted. Cells were treated with different concentrations of SA. Aliquots of culture were taken at 0 (before treatment) and 5 min, and p48 SIP kinase activities were assayed using myelin basic protein (MBP) as a substrate. Data presented are fold of induction relative to the basal kinase activity at time zero. Data presented in all panels described above are from one of at least three independent experiments with similar results.

In FIG. 4A, extracts prepared from cells treated with 250 μM SA or 2 mM $H_2O_2$ for 10 minutes or 30 minutes were separated on a 10% SDS-PAGE gel. Proteins were then transferred to nitrocellulose membranes and phosphotyrosine-containing proteins were detected by immunoblot analysis using the phosphotyrosine-specific monoclonal antibody 4G10. The band corresponding to the p48 SIP kinase is marked with an asterisk (*) while bands corresponding to other proteins of 58 kDa, 52 kDa, and 40 kDa are marked with a dot (•). In FIG. 4B, phosphorylation of tyrosine residues of the p48 SIP kinase was confirmed and the specificity of the phosphotyrosine monoclonal antibody 4G10 was tested by immunoprecipitation coupled with the in-gel kinase activity assay. Phosphotyrosine-containing proteins in total cell extracts were immunoprecipitated with 4G10 in the absence of competitor (lanes 1 to 6) or in the presence of 1 mM of either phosphoserine (P-Ser, lanes 7 and 10), phosphothreonine (P-Thr, lanes 8 and 11), or phosphotyrosine (P-Tyr, lanes 9 and 12). Kinase activities in the complexes were determined using the in-gel kinase assay. When the 4G10 antibody was omitted from the precipitation reaction, no kinase activity was precipitated from the protein extracts. Molecular mass markers at left are given in kDa.

In FIG. 5A tobacco leaves were injected with either 500 μM SA or water. At the indicated times leaf discs were taken and total protein extracts were prepared. Kinase activities were monitored with MBP as a substrate. FIG. 5B shows the results of a double injection experiment in which tobacco leaves were first injected with water and 4 hours later the same leaves were injected with either SA or water. Leaf discs were taken at the indicated times and kinase activities were assayed. In FIG. 5C, quantitation of the p48 kinase activities shown in FIG. 5A were performed with a phosphoimager (●, SA injected; ○, water injected). Kinase activities were normalized to the level detected at zero time, which was assigned a value of 1. In FIG. 5D the 48 kDa kinase activities shown in FIG. 5B were quantitated with a phosphoimager (●, second injection was SA; ○, second injection was water). The slightly lower band of kinase activity seen in FIG. 5A and FIG. 5B at about 44 kDa (compare FIG. 6), which is poorly resolved from 48 kDa kinase, was not included in quantitation for FIGS. 5C and 5D. Arrows indicate the time of injection.

In FIG. 6C, quantitation of p48 SIP kinase activities (●, TMV inoculated; ○, mock inoculated) and 44 kDa kinase activities (▲, TMV inoculated; △, mock inoculated) shown in FIG. 6A and FIG. 6B was performed with a phosphoimager. Kinase activities were normalized to the level of the p48 kinase present at zero time, which was assigned a value of 1. The position of the p48 SIP kinase is denoted with an asterisk (*) while that of the 44 kDa kinase is marked with a dot (•). Molecular mass markers at left are given in kDa.

FIG. 8A: after the ultracentrifugation step, protein samples prepared simultaneously from either SA-treated cells (●) or control water-treated cells (○) were loaded onto a HiTrapQ column connected to a fast protein liquid chromatography system. The column was then eluted with a NaCl gradient, depicted by the dashed lines. Kinase activity was determined by the in-solution kinase assay, using MBP as substrate. FIG. 8B: selected fractions from the HiTrapQ column chromatography of the protein sample from SA-treated cells were assayed by the in-gel kinase method, with MBP as the substrate. The position of the molecular mass markers in kDa is indicated at left.

FIG. 9A: for protein composition analysis, an aliquot of protein sample from each step of the purification was separated on a 10% SDS-polyacrylamide gel and stained with Coomassie blue. Lane 1 contains the 10-kDa size marker (Gibco BRL); lane 2, crude extract (20 μg); lane 3, 0 to 30% ammonium sulfate fraction (10 μg); lane 4, supernatant after 130,000 g ultracentrifugation (10 μg); lane 5, pooled fractions from the Q-Sepharose column (5 μg); lane 6, pooled fractions from the phenyl-Sepharose column (5 μg); lane 7, pooled fractions from the MonoQ HR 5/5 column (2.5 μg); lane 8, pooled fractions from the MBP-Sepharose affinity column (1 μg); lane 9, pooled fractions from the poly-L-lysine agarose (1 μg); and lane 10, pooled fractions from the Superdex 200 HR 10/30 column (0.5 μg). The position of molecular mass markers in kDa is indicated at left. FIG. 9B: to determine the size of the purified enzyme, 1 unit was loaded on a 10% SDS-polyacrylamide gel embedded with MBP, and the kinase activity was detected by using an in-gel assay. FIG. 9C: For analysis of phosphotyrosine-containing proteins, samples from each purification step were subjected to SDS-PAGE, blotted, and probed with anti-phosphotyrosine monoclonal antibody 4G10. Lane 1 contains crude extract (5 µg); lane 2, 0 to 30% ammonium sulfate fraction (5 µg); lane 3, supernatant after 130,000 g ultracentrifugation (5 µg); lane 4, pooled fractions from the Q-Sepharose column (5 µg); lane 5, pooled fractions from the phenyl-Sepharose column (1 µg); lane 6, pooled fractions from the MonoQ HR 5/5 column (0.5 µg); lane 7, pooled fractions from the MBP-Sepharose affinity column (5 units, ~47 ng); lane 8, pooled fractions from the poly-L-lysine agarose (5 units, ~29 ng); and lane 9, pooled fractions from the Superdex 200 HR 10/30 column (5 units, ~15 ng).

FIG. 14 illustrates an alignment of the deduced amino acid sequence of the SIP kinase (SIPK) with other members of the tobacco MAP kinase family, as well as stress-related MAP kinases from other plants. The amino acid sequences of Ntf3, Ntf4, Ntf6 (Wilson et al., 1993, 1995) and WIPK (Seo et al., 1995) from tobacco, MsK7 (Duerr et al., 1993; Jonak et al., 1993) and MMK4 (Jonak et al., 1996) from alfalfa, and AtMPK3 (Mizoguchi et al., 1993) from Arabidopsis were deduced from cDNA sequences. Numbers within parentheses indicate the percentage of identity to the SIP kinase. Dots represent amino acid residues that match the SIP kinase, and dashes indicate gaps introduced to maximize alignment. The conserved TEY phosphorylation motif for MAP kinase in underlined. The unique proline residue in the conserved kinase subdomain VIII of SIP kinase is marked with an asterisk. Roman numerals indicate the 11 major conserved subdomains of serine/threonine protein kinases. The six peptide sequences obtained by miscrosequencing are shown on top of the SIP kinase sequence. The boundary between peptides 5 and 6 is indicated by a vertical line.

DETAILED DESCRIPTION OF THE INVENTION

Figure 1A:
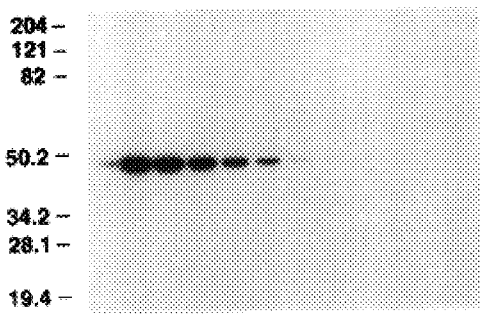
FIGS. 1A–1E are a series of autoradiographs and two graphs illustrating the phosphorylation events catalyzed by the SA-induced protein (SIP) kinase of the present invention. The results presented indicate that salicylic acid activates a 48 kDa kinase which preferentially uses myelin basic protein (MBP) as a substrate. Tobacco suspension culture cells were treated by addition of either 250 µM of SA (FIG. 1A) or an equal volume of water (FIG. 1B) as a negative control. Aliquots of each culture were taken at the indicated times, and kinase activity in total cell extracts was tested with an in-gel kinase activity assay using MBP as a substrate.

The present invention is directed to a novel protein kinase isolated from plants which is rapidly and transiently activated by salicylic acid, as well as by hydrogen peroxide or infection with tobacco mosaic virus (TMV). Transgenic plants with altered expression of this kinase are expected to demonstrate enhanced disease resistance to certain pathogens. The novel protein kinase of the present invention is sometimes referred to herein as "SIP kinase" or "p48 SIP kinase" to denote its novel functional features (activatable by agents, such as SA, that induce a resistance response) and approximate molecular weight as isolated from tobacco.

I. Definitions

Various terms relating to the biological molecules of the present invention are used hereinabove and also throughout the specifications and claims. The terms "substantially the same," "percent similarity" and "percent identity" are defined in detail below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules of the invention the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest (e.g., SIP kinase), but which do not substantially recognize and bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "pathogen-inoculated" refers to the inoculation of a plant with a pathogen.

The term "promoter region" refers to the 5' regulatory regions of a gene. In the present invention, the use of CaMV 35S gene promoters and/or tetracycline repressor/operator gene promoters is contemplated.

The term "selectable" marker gene refers to a gene product that when expressed confers a selectable phenotype such as antibiotic resistance on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "DNA construct" refers to genetic sequence used to transform plants and generate progeny transgenic plants. These constructs may be administered to plants in a viral or plasmid vector. Other methods of delivery such as Agrobacterium T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1995.

II. Characterization of SA-Induced MAP Kinase (SIP Kinase)

Numerous studies have demonstrated that SA is an endogenous signal for the activation of several plant defense responses, including the synthesis of PR proteins (Klessig and Malamy, 1994; Ryals et al., 1994, 1996). However, many of the components in the SA signal transduction pathway remain to be elucidated. It has now been discovered in accordance with the present invention that a plant protein kinase of about 48 kDa in molecular weight is rapidly activated by treatment with SA.

The activation of p48 SIP kinase by SA was rapid and transient, with activity returning to basal levels within 45 minutes after stimulation. A second addition of SA at up to 4 hr after the initial treatment did not reactivate the SIP kinase, suggesting that the activation pathway was desensitized. Without the invention being limited by any proposed mechanism, it is possible that a negative regulatory loop is responsible for the transient nature of the activation and the subsequent refractory period. In mammalian systems, inactivation of MAP kinases is performed by a dual specificity protein (MAP kinase phosphatases), which simultaneously dephosphorylate both the threonine and tyrosine residues of MAP kinases with high efficiency (Keyse, 1995; Groom et al., 1996). Transcription of these MAP kinase phosphatases is quickly activated by the MAP kinase signaling pathway (Bokemeyer et al., 1996).

Figure 3:
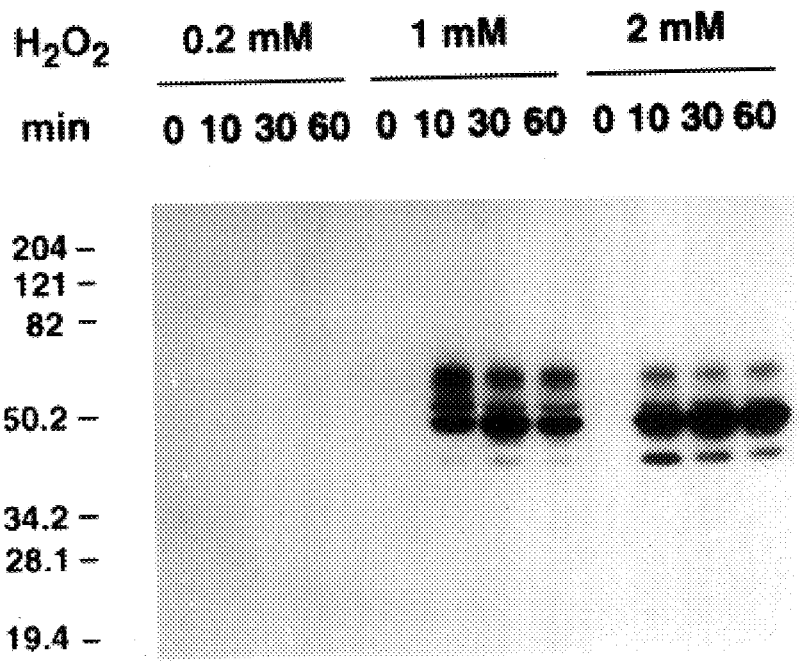
FIG. 3 is an autoradiograph illustrating that hydrogen peroxide treatment activates several kinases, including the p48 SIP kinase. Cells were treated with different concentrations of $H_2O_2$ for varying lengths of time as indicated. Total cell extracts were prepared and kinase activities were assayed using MBP as a substrate. The asterisk (*) indicates the position of the p48 SIP kinase. Molecular mass markers at left are given in kilodaltons. With a long exposure of the autoradiogram, two weakly induced kinase activity bands were also detected at 200 kDa and 75 kDa.

Several kinases were activated in cells exposed to exogenous $H_2O_2$. See FIG. 3. In addition, at least four proteins were phosphorylated on tyrosine residues in response to $H_2O_2$. See FIG. 4. Using immunoprecipitation coupled with an in-gel kinase assay, it was demonstrated that one of these proteins is the p48 SIP kinase. The sizes of the other $H_2O_2$-activated kinases (58 kDa, 52 kDa and 40 kDa) as shown in FIG. 3, were consistent with those of tyrosine phosphorylated proteins; however in contrast to the SIP kinase, they were not immunoprecipitable with the anti-phosphotyrosine antibody.

The mechanism by which SA activates the p48 SIP kinase has not yet been fully elucidated. However, without being limited by the following hypothesis, it is believed that, since SA can inhibit the two major $H_2O_2$-scavenging enzymes (Chen et al., 1993; Durner and Klessig, 1995) and generate radicals (Durner and Klessig 1996), as well as function as an antioxidant (Halliwell et al., 1995), it may activate the SIP kinase by altering the redox status of the cell.

The p48 SIP kinase can be activated by TMV infection. The TMV-induced elevation in p48 SIP kinase activity correlates with increases in endogenous SA levels. Thus, this p48 SA-inducible kinase is involved in the signaling pathway that regulates the induction of certain defense responses after pathogen attack.

Several lines of evidence indicate that the SIP kinase of the invention is a member of the MAP kinase family: (1) activation of the SIP kinase is associated with phosphorylation of a tyrosine residue(s); (2) the SIP kinase preferentially phosphorylates the myelin basic protein (MBP); (3) the SIP kinase is unable to use GTP as a phosphate donor; (4) the SIP kinase lacks a calcium requirement for activity; and (5) the size of the SIP kinase (about 48 kDa as isolated from tobacco) is within the 38 to 55 kDa size range of known members of the MAP kinase family from many organisms (Seger and Krebs, 1995).

To confirm that the SIP kinase is indeed a novel MAP kinase, the kinase was purified and the amino acid sequence of several tryptic peptides were used to isolate its encoding cDNA. The nucleotide and deduced amino acid sequence of the SIP kinase-encoding cDNA exhibits high homology to other cloned MAP kinases, particularly the tobacco Ntf4 MAP kinase. Furthermore, SIP kinase contains the TEY phosphorylation sequence and conserved kinase catalytic domain associated with serine/threonine kinases. However, SIP kinase possesses a unique amino-terminal sequence, as well as a proline in place of alanine in the conserved kinase subdomain VIII (see FIG. 14). All other MAP kinases cloned from plants, yeast and mammals have an alanine at this position. Thus, SIP kinase clearly is a new member of the MAP kinase family.

A tobacco clone that encodes an exemplary SIP kinase of the invention is described in detail herein. The nucleotide sequence of a cDNA encoding tobacco SIP kinase is set forth below as Sequence I.D. No. 1. It is believed that Sequence I.D. No. 1 constitutes a full-length SIP kinase-encoding clone as it contains a suitable methionine for initiation of translation. Furthermore, expression of this cDNA in *E. coli* results in production of a protein that phosphorylates MBP (note MAP kinases have low basal phosphorylation activity in the absence of their activation by the MAP kinase kinases).

The tobacco SIP kinase cDNA shown below is approximately 1.54 kb in length.

Sequence I.D. No. 1 (5' → 3'):

CACAATTCCA CATATTCATT GACATACTAC GGCCCTTCTT

CCCTAATTTT AAGACAAAGG AAAAAAAGTA ATTATTGATT

CTTCTAGGAT TTACAATTTT TGTTGACGAA TTTTCCAAAA

AAAAAAATAT GGATGGTTCT GGTCAGCAGA CGGACACGAT

GATGTCTGAT GCGGGGCGG AGCAGCCACC TACGGCGCCG

CAGCCGGTGG CCGGTATGGA TAATATTCCG GCGACGTTGA

GCCACGGTGG CAGGTTCATT CAATACAATA TATTTGGTAA

TATATTTGAA GTTACTGCTA AATATAAGCC TCCTATTTTG

CCTATTGGTA AAGGTGCTTA CGGCATCGTT TGTTCTGCTT

TGAACTCGGA GACAATTGAG AACGTAGCGA TAAAGAAAAT

CGCAAATGCT TTTGATAACA AGATTGATGC CAAGAGGACT

TTGAGAGAGA TCAAGCTTCT TCGGCATATG GATCATGAAA

ACATTGTTGC GATCAGAGAT ATAATTCCAC CACCACAGAG

AGAGGCCTTT AATGATGTTT ATATTGCGTA TGAGCTTATG

GATACTGATC TCCATCAAAT TATTCGCTCT AATCAGGGTT

TATCTGAGGA GCACTGTCAG TATTTCTTGT ATCAGATCCT

CCGAGGGTTG AAATACATAC ATTCTGCGAA TGTTCTGCAC

AGGGACTTGA AGCCTAGCAA TCTCCTGTTG AATGCCAACT

GTGATTTAAA GATATGTGAT TTTGGGCTAG CTCGTGTCAC

TTCTGAAACT GACTTTATGA CGGAATATGT TGTGACAAGA

TGGTATCGTC CACCTGAGCT GTTGTTAAAT TCGTCTGACT

ATACTGCAGC AATTGACGTA TGGTCAGTGG GTTGCATTTT

CATGGAATTG ATGGACAGGA AACCCCTATT TCCTGGTAGA

GATCACGTAC ACCAGCTGCG TCTTATTATG GAGTTGATTG

GTACTCCTTC AGAGGCTGAA ATGGAGTTTT TAAATGAGAA

TGCAAAACGA TACATCCGCC AACTTCCTCT TTACCGTCGA

CAATCATTCA CTGAAAAGTT TCCACATGTA CACCCAACTG

CAATTGATCT TGTCGAGAAA ATGCTGACAT TTGATCCTAG

AAGGAGAATA ACAGTTGAAG GTGCACTTGC ACATCCTTAC

CTGAACTCGC TCCACGATAT TAGTGACGAG CCCATTTGCA

TGACTCCCTT TAGCTTCGAC TTTGAACAGC ATGcCCTTAC

GGAGGAACAG ATGAAGGAGC TGATTTACAG GGAGTCGCTT

GCATTTAATC CTGAATACCA GCATATGTGA ATAATTGCTG

GTAAGATTGT TGTCAGTTTG ATCTCCAACT GACAATTTGT

CCCTCCATGT ATATATGTGT GCACTTCGTC CGAAACACGG

ATGGCTTTCT TATGCAAACA CTTAGTTATG AAGCTGATTT

-continued

GTGTAAAGAA TTGTTTGATG TATCTGATGA GGTGGATCGC

TTGTATTGGT TCTGTTTTAA TTTACTGAAG TCATAGTGGA

CGAAAAAAAA AAAAAAAAAA AAAA

The amino acid sequence deduced from Sequence I.D. No. 1 is set forth herein as Sequence I.D. No. 2. Sequence I.D. No. 2 is shown in FIG. 14 aligned with amino acid sequences of other cloned MAP kinases. The corresponding Sequence I.D. Numbers are as follows: SIPK is Sequence I.D. No. 2 (as mentioned); Ntf4 is Sequence I.D. No. 3, Msk7 is Sequence I.D. No. 4; WIPK is Sequence I.D. No. 5, MMK4 is Sequence I.D. No. 6; AtMPK3 is Sequence I.D. No. 7; Ntf6 is Sequence I.D. No. 8; and Ntf3 is Sequence I.D. No. 9. FIG. 14 also shows the peptide fragments of purified tobacco SIP kinase obtained by tryptic digestion, as described in Example 2. The Sequence I.D. Numbers of these fragments are as follows: Peptide 1 is Sequence I.D. No. 10; Peptide 2 is Sequence I.D. No. 11, Peptide 3 is Sequence I.D. No. 12, Peptide 4 is sequence I.D. No. 13, Peptide 5 & 6 together are Sequence I.D. No. 14.

Although the tobacco SIP kinase is described and exemplified herein, this invention is intended to encompass nucleic acid sequences and proteins from other species that are sufficiently similar to be used interchangeably with tobacco SIP kinase-encoding nucleic acids and proteins for the purposes described below. Because of the high degree of conservation of genes encoding specific MAP kinases, it will be appreciated by those skilled in the art that SIP kinase-encoding nucleic acids from diverse species, and particularly higher plant species, should possess a sufficient degree of homology with tobacco SIP kinase so as to be interchangeably useful in various applications. The present invention, therefore, is drawn to SIP kinase-encoding nucleic acids and encoded proteins from any species in which they are found, preferably to SIP kinases of plant origin, and most preferably to SIP kinases of higher plant origin. Accordingly, when the terms "SIP kinase" and "p48 SIP kinase" are used herein, they are intended to encompass all SIP kinases falling within the confines of homology set forth below, of which tobacco SIP kinase is an exemplary member.

MAP kinases are activated post-translationally by phosphorylation. The SIP kinase of the invention is also unique in the manner by which it is activated (MAP kinases are activated post-translationally by phosphorylation, but the agents that trigger that activation differ among various MAP kinases). The tobacco SIP kinase exemplified herein is activated by SA, $H_2O_2$, and TMV infection, all of which share a common feature of being agents that induce a disease defense response in plants (defined above in the Summary of the Invention). Accordingly, in the same manner that structural homologs of tobacco SIP kinase are considered to be within the scope of this invention, functional homologs, as pertains to activation of the kinase, are also considered to be within the scope of this invention. Such "activation" homologs include SIP kinases that are activated by a variety of agents known to induce a disease defense response in plants, preferably via the salicylic acid signal transduction pathway. Examples of plant disease defense responses include, but are not limited to, production of low molecular weight compounds with antimicrobial activity (referred to as phytoalexins) and induction of expression of defense (or defense-related) genes, whose products include, for example, peroxidases, cell wall proteins, proteinase inhibitors, hydrolytic enzymes, pathogenesis-related (PR)

proteins and phytoalexin biosynthetic enzymes, such as phenylalanine ammonia lyase and chalcone synthase (Dempsey and Klessig, 1995). Such defense responses appear to be induced in plants by several signal transduction pathways involving secondary defense signaling molecules produced in plants (see below). Certain of these defense response pathways are SA dependent, while others are partially SA dependent and still others are SA independent. For this reason, the SIP kinases of the present invention preferably are activated by agents which induce a disease defense response via the SA signal transduction pathway in plants.

Agents that induce disease defense responses in plants include, but are not limited to: (1) microbial pathogens, such as fungi, bacteria and viruses; (2) microbial components and other defense response elicitors, such as proteins and protein fragments, small peptides, β-glucans, elicitins and harpins (see Benhamou, 1996), cryptogein (see Ricci et al., 1989) and oligosaccharides (see John et al., 1997); and (3) secondary defense signaling molecules produced by the plant, such as SA, $H_2O_2$, ethylene and jasmonates (see Yang et al., 1997).

Allelic variants and natural mutants of Sequence I.D. No. 1 are likely to exist within the plant genome and within the genomes of other species. Because such variants are expected to possess certain differences in nucleotide and amino acid sequence, this invention provides an isolated SIP kinase-encoding nucleic acid molecule having at least about 75% (and preferably over 80%) sequence homology in the coding region with the nucleotide sequence set forth as Sequence I.D. No. 1 (and, most preferably, specifically comprising the coding region of sequence I.D. No. 1). This invention also provides an isolated SIP kinase having at least about 93% (preferably 95% or greater) sequence homology with the amino acid sequence of Sequence I.D. No. 2. Because of the natural sequence variation likely to exist among SIP kinases and nucleic acids encoding them, one skilled in the art would expect to find up to about 25–30% nucleotide sequence variation, while still maintaining the unique properties of the SIP kinase of the present invention. Such an expectation is due in part to the degeneracy of the genetic code, as well as to the known evolutionary success of conservative amino acid sequence variations, which do not appreciably alter the nature of the protein. Accordingly, such variants are considered substantially the same as one another and are included within the scope of the present invention.

For purposes of this invention, the term "substantially the same" refers to nucleic acid or amino acid sequences having sequence variation that do not materially affect the nature of the protein (i.e. its activation by pathogens or other agents, such as SA, that induce plant defense responses, such as PR gene expression, its structure and/or biological activity). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure, function or activation by disease resistance-inducing pathogens or agents (e.g., SA). The terms "percent identity" and "percent similarity" are also used herein in comparisons among amino acid sequences. These terms are intended to be defined as they are in the UWGCG sequence analysis program (Devereaux et al., Nucl. Acids Res. 12: 387–397, 1984), available from the University of Wisconsin.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") are used.

III. Preparation of SIP Kinase-Encoding Nucleic Acid Molecules, SIP Kinase Protein and Antibodies Against SIP Kinase A. Nucleic Acid Molecules Nucleic acid molecules encoding the SIP kinase of the invention may be prepared by two general methods: (1) They may be synthesized from appropriate nucleotide triphosphates, or (2) they may be isolated from biological sources. Both methods utilize protocols well known in the art.

The availability of nucleotide sequence information, such as the full length cDNA having Sequence I.D. No. 1, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 1.54 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 1.54 kb double-stranded molecule. A synthetic DNA molecule so constructed may then be cloned and amplified in an appropriate vector.

Nucleic acid sequences encoding SIP kinase may be isolated from appropriate biological sources using methods known in the art. In a preferred embodiment, a cDNA clone is isolated from a tobacco cDNA library. In an alternative embodiment, genomic clones encoding SIP kinase may be isolated. Alternatively, cDNA or genomic clones encoding SIP kinase from other species, preferably higher plant species, may be obtained.

In accordance with the present invention, nucleic acids having the appropriate level sequence homology with the coding region of Sequence I.D. No. 1 may be identified by using hybridization and washing conditions of appropriate stringency. For example, hybridizations may be performed, according to the method of Sambrook et al., using a hybridization solution comprising: 5× SSC, 5× Denhardt's reagent, 1.0% SDS, 100 μg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2× SSC and 1% SDS; (2) 15 minutes at room temperature in 2× SSC and 0.1% SDS; (3) 30 minutes-1 hour at 37° C. in 1× SSC and 1% SDS; (4) 2 hours at 42–65° in 1× SSC and 1% SDS, changing the solution every 30 minutes. Alternatively, the hybridization procedure described in Example 2 may be used.

Nucleic acids of the present invention may be maintained as DNA in any convenient cloning vector. In a preferred embodiment, clones are maintained in plasmid cloning/expression vector, such as pGEM-T (Promega Biotech, Madison, Wis.) or pBluescript (Stratagene, La Jolla, Calif.), either of which is propagated in a suitable *E. coli* host cell.

SIP kinase-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1. Such oligonucleotides are useful as probes for detecting SIP kinase genes or mRNA in test samples of plant tissue or other biological sources, e.g. by PCR amplification, or for the positive or negative regulation of expression of SIP kinase genes at or before translation of the mRNA into proteins.

B. Proteins

A SIP kinase protein of the present invention may be prepared in a variety of ways, according to known methods. The protein may be purified from appropriate sources, e.g., cultured plant cells or tissues as described in detail in Examples 1 and 2. Those Examples describe the isolation of SIP kinase from cultured tobacco cell suspensions, followed by its purification to apparent homogeneity by ammonium sulfate fractionation, ultracentrifugation and six column chromatography steps.

Alternatively, the availability of nucleic acids molecules encoding SIP kinase enables production of the protein using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

According to a preferred embodiment, larger quantities of SIP kinase may be produced by expression in a suitable procaryotic or eucaryotic system. For example, part or all of a DNA molecule, such as the cDNA having Sequence I.D. No. 1, may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The SIP kinase produced by gene expression in a recombinant procaryotic or eucarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The SIP kinase of the invention, prepared by the aforementioned methods, may be analyzed according to standard procedures. Methods for analyzing the physical characteristics and biological activity of SIP kinase are set forth in Examples 1 and 2.

The present invention also provides antibodies capable of immunospecifically binding to proteins of the invention. Polyclonal or monoclonal antibodies directed toward SIP kinase may be prepared according to standard methods. Monoclonal antibodies may be prepared according to general methods of Köhler and Milstein, following standard protocols.

In a preferred embodiment, antibodies are prepared, which react immunospecifically with various epitopes of SIP kinase. In a particularly preferred embodiment, polyclonal antibodies have been generated against each of two synthetic peptide corresponding to (1) the tobacco SIP kinase N-terminal sequence (residues 1–24 of Sequence I.D. No. 2; FIG. 14) or (2) the tobacco SIP kinase C-terminal sequence (residues 376–393 of Sequence I.D. No. 2; FIG. 14). The anti-N-terminus antibody was found to be immunologically specific for SIP kinase (it did not recognize Ntf4 or WIPK). The anti C-terminus antibody is immunologically specific for SIP kinase and for Ntf4, but does not recognize WIPK.

Polyclonal or monoclonal antibodies that immunospecifically interact with SIP kinase can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-SIP kinase antibodies are described below.

IV. Uses of SIP Kinase-Encoding Nucleic Acids, SIP Kinase Protein and Antibodies The potential of recombinant genetic engineering methods to enhance disease resistance in agronomically important plants has received considerable attention in recent years. Protocols are currently available for the stable introduction of genes into plants, as well as for augmentation of gene expression. The present invention provides nucleic acid molecules which, upon stable introduction into a recipient plant, enhance the plant's ability to resist pathogen attack. SIP kinase proteins of the invention may also be used as a research tool to identify other proteins involved in the hypersensitive response and/or systemic acquired resistance response in plants.

A. SIP Kinase-Encoding Nucleic Acids

SIP kinase-encoding nucleic acids may be used for a variety of purposes in accordance with the present invention. SIP kinase-encoding DNA, RNA, or fragments thereof may be used as probes to detect the presence of and/or expression of genes encoding SIP kinase. Methods in which SIP kinase-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The SIP kinase-encoding nucleic acids of the invention may also be utilized as probes to identify related genes either from plants or from other species. As is well known in the art, hybridization stringencies may be adjusted to allow hybridization of nucleic acid probes with complementary sequences of varying degrees of homology. Thus, SIP kinase-encoding nucleic acids may be used to advantage to identify and characterize other genes of varying degrees of relation to SIP kinase, thereby enabling further characterization the signalling cascade involved in the disease resistance response in plants. Additionally, they may be used to identify genes encoding proteins that interact with SIP kinase (e.g., by the "interaction trap" technique), which should further accelerate elucidation of these cellular signalling mechanisms.

Nucleic acid molecules, or fragments thereof, encoding SIP kinase may also be utilized to control the production of SIP kinase, thereby regulating the amount of protein available to participate in disease resistance signalling pathways. Alterations in the physiological amount of SIP kinase may act synergistically with other agents used to protect plants during pathogen attack. In one embodiment, the nucleic acid molecules of the invention may be used to decrease expression of SIP kinase in plant cells. In this embodiment, full-length antisense molecules are employed which are targeted to SIP kinase, or antisense oligonucleotides, targeted to specific regions of SIP kinase-encoding genes that are critical for gene expression, are used. The use of antisense molecules to decrease expression levels of a predetermined gene is known in the art. In a preferred embodiment, antisense oligonucleotides are modified in various ways to increase their stability and membrane permeability, so as to maximize their effective delivery to target cells in vitro and in vivo. Such modifications include the preparation of phosphorothioate or methylphosphonate derivatives, among many others, according to procedures known in the art.

In another embodiment, overexpression of SIP kinase is induced to generate a co-suppression effect. This excess expression serves to promote down-regulation of both endogenous and exogenous SIP kinase-encoding genes. Under other circumstances, overexpression can lead to overproduction of SIP kinase. Overproduction of SIP kinase in transgenic plants may be assessed by immunofluorescence or other standard techniques known in the art. Alternatively, overproduction of SIP kinase in transgenic plants or plant cells may facilitate the isolation and characterization of other components involved in protein-protein complex formation occurring during the disease resistance response in plants.

As described above, SIP kinase-encoding nucleic acids are also used to advantage to produce large quantities of substantially pure SIP kinase protein, or selected portions thereof.

B. SIP Kinase Protein and Antibodies

Purified SIP kinase, or fragments thereof, may be used to produce polyclonal or monoclonal antibodies which also may serve as sensitive detection reagents for the presence and accumulation of SIP kinase (or complexes containing SIP kinase) in cultured plant cells or tissues and in intact plants. Recombinant techniques enable expression of fusion proteins containing part or all of the SIP kinase protein. The full length protein or fragments of the protein may be used to advantage to generate an array of monoclonal or polyclonal antibodies specific for various epitopes of the protein, thereby providing even greater sensitivity for detection of the protein in cells or tissue.

Polyclonal or monoclonal antibodies immunologically specific for SIP kinase may be used in a variety of assays designed to detect and quantitate the protein. Such assays include, but are not limited to: (1) flow cytometric analysis; (2) immunochemical localization of SIP kinase in cultured cells or tissues; and (3) immunoblot analysis (e.g., dot blot, Western blot) of extracts from various cells and tissues. Additionally, as described above, anti-SIP kinase can be used for purification of SIP kinase (e.g., affinity column purification, immunoprecipitation).

C. Transgenic Plants

Transgenic plants constitutively expressing SIP kinase gene would be generated using standard transformation methods known to those skilled in the art. Presumably, these plants would have altered resistance to pathogens as the SIP kinase has been shown to be activated during a resistance response to TMV infection. The SIP kinase gene would be placed under a powerful constitutive promoter like the Cauliflower Mosaic Virus (CaMV) 35S promoter and introduced into plants using procedures such as Agrobacterium-mediated transformation. Expression of the kinase would be modified by ectopic, overexpression of the gene under control of the CaMV 35S promoter.

Alternatively SIP kinase expression would also be disrupted by the expression of the gene in an antisense orientation under the CaMV 35S promoter.

Transgenic plants expressing the SIP kinase gene under an inducible promoter are also contemplated to be within the scope of the present invention. Inducible plant promoters include the tetracycline repressor/operator controlled promoter.

Optionally, transgenic plants would be created containing mutations in the region encoding the active site of SIP kinase. This embodiment is preferred over the use of antisense constructs due to the very high homology between MAP kinases. For example, a mutated p48 SIP kinase with a Lys to Arg change in the kinase subdomain II has been made, and could be introduced into wild tobacco plants. This mutation would block the phosphate transfer from ATP to the protein substrate, thereby rendering the kinase permanently inactive (the Lys to Arg mutant SIP kinase produced in *E. coli* has lost the basal phosphorylation activity found with its wildtype counterpart recombinant protein). Since the mutant p48 kinase would still serve as the substrate for upstream MAP kinase kinase and physically compete with the wild-type p48 SIP kinase, but would not transduce signal to downstream components, it may be possible to specifically block the pathway without affecting other MAP kinase cascades.

From the foregoing discussion, it can be seen that SIP kinase-encoding nucleic acids and SIP kinase proteins and antibodies of the invention can be used to detect SIP kinase gene expression and protein accumulation for purposes of assessing the genetic and protein interactions involved in the plant disease resistance response. It is also anticipated that SIP kinase-encoding nucleic acid molecules and transgenic plants containing them will be useful for the regulation of the disease resistance pathway in plants and for enhancing resistance to plant pathogens.

The following examples are intended to illustrate embodiments of the invention. They are not intended to limit the scope of the invention in any way.

EXAMPLE I

IDENTIFICATION AND CHARACTERIZATION OF SIP KINASE FROM TOBACCO

This example describes the identification of SIP kinase protein from tobacco suspension cultures, and characterization of its activity.

MATERIALS AND METHODS

A. Treatment of Tobacco Cell Suspension Culture

The cell suspension culture was derived from callus tissue originated from leaves of *Nicotiana tabacum* cv Xanthi nc and grown in MS medium supplemented with 1 mg/L α-naphthaleneacetic acid, 0.1 mg/L 2,4-dichlorophenoxyacetic acid, 0.1 mg/L benzyladenine, and 3% sucrose. Log phase cells were used three days after a 1:10 dilution. Treatment with $H_2O_2$, SA and its analogues was performed in the original flasks in the dark to avoid any stresses associated with transfer. At various times, 10 mL cells (approximately 0.2 to 0.3 g fresh weight of cells) were harvested by filtration. The cells were quickly frozen in liquid nitrogen and stored at −80° C. until analysis.

B. Infection and Treatment of Tobacco Leaves

Tobacco plants (*N. tabacum* cv Xanthi nc) were grown at 22° C. in a growth room programmed for a 14-hr light cycle. Plants approximately 7–8 weeks old were used for experiments. For temperature-shift experiments, plants were transferred to a 32° C. chamber one day before inoculation. TMV strain U1 was used at a concentration of 1 μg/mL in 50 mM phosphate buffer, pH 7.0; mock inoculation was done with buffer only. After 48 hours infected plants were shifted back to 22° C. and leaf discs (1 cm in diameter) were taken at the indicated times. For water or SA treatment, one leaf from each plant was injected with solution using a syringe until the entire leaf was infiltrated. At various times, leaf discs were taken, quickly frozen in liquid nitrogen, and stored at −80° C. until analysis.

C. Preparation of Protein Extracts

Leaf discs were first ground to a fine powder in 1.5 ml microcentrifuge tubes using small plastic pestles. After adding 0.25 mL extraction buffer (100 mM Hepes, pH 7.5, 5 mM EDTA, 5 mM EGTA, 10 mM DTT, 10 mM $Na_3VO_4$, 10 mM NaF, 50 mM β-glycerolphosphate, 1 mM phenylmethylsulfonyl fluoride, 5 μg/mL antipain, 5 μg/mL aprotinin, 5 μg/mL leupeptin, 10% glycerol, 7.5% polyvinylpolypyrrolidone), the mixture was sonicated for 15 seconds with a W-375 Sonicator (Heat System-Ultrasonics, Inc., N.Y.) fitted with a microprobe at setting 4 and 80% duty cycle. To prepare extracts from treated cells, cells were mixed with two volumes (w/v) of extraction buffer and were then sonicated twice for 15 seconds each in 1.5 mL microcentrifuge tube. After centrifugation at 13,000 rpm for 20 minutes, supernatants were transferred into clean tubes, quickly frozen in liquid nitrogen and stored at −80° C.

D. Protein Concentration Assay

The concentration of protein extracts was determined using the Bio-Rad protein assay kit (Bio-Rad, CA) according to manufacturer's instructions with BSA as standard.

E. In-gel Kinase Activity Assay

The in-gel kinase assay was performed as described previously (Zhang et al., 1993). Extracts containing 10 μg protein were electrophoresed on 10% SDS-polyacrylamide gels imbedded with either 1 mg/mL of casein, 1 mg/mL histone (Type III-SS, Sigma, MO), 1 mg/mL BSA, or 0.25 mg/mL of MBP in the separating gel as substrate for the kinase. After electrophoresis, SDS was removed by washing the gel with washing buffer (25 mM Tris, pH 7.5, 0.5 mM DTT, 0.1 mM $Na_3VO_4$, 5 mM NaF, 0.5 mg/mL BSA, 0.1% Triton X-100 [v/v]). The buffer was changed three times, each for 30 minutes at room temperature. The kinases were allowed to renature in 25 mM Tris, pH 7.5, 1 mM DTT, 0.1 mM $Na_3VO_4$, 5 mM NaF at 4° C. overnight with three changes of buffer. The gel was then incubated at room temperature in 30 mL reaction buffer (25 mM Tris, pH 7.5, 2 mM EGTA, 12 mM $MgCl_2$, 1 mM DTT, 0.1 mM $Na_3VO_4$) with 200 nM ATP plus 50 μCi γ-$^{32}$P-ATP (3000 Ci/mmole) for 60 minutes. The reaction was stopped by transferring the gel into 5% TCA(w/v)/1% NaPPi (w/v). The unincorporated γ-$^{32}$P-ATP was removed by washing in the same solution for at least 6 hours with 5 changes of buffer. The gel was dried onto 3 MM paper and exposed to Kodak XAR-5 film. Prestained size markers (Bio-Rad, CA) were used to calculate the size of the kinases. Quantitation of the relative kinase activities were done using a phosphoimager (Molecular Dynamics Inc., CA).

F. Immunoblot Analysis With Anti-phosphotyrosine Antibody

Protein extracts were separated by SDS-PAGE on 10% acrylamide gels, and the proteins were transferred to nitrocellulose membrane by semidry electroblotting. The membrane was blocked for 2 hours in TBS buffer (20 mM Tris, pH 7.5, 150 mM NaCl, 0.1% Tween 20, 0.1 mM $Na_3VO_4$) with 10% BSA at room temperature, and then incubated with the phosphotyrosine-specific monoclonal antibody 4G10 (Upstate Biotechnology Incorporated, NY) in TBS buffer with BSA for 1 hr. After the blot was incubated with horseradish peroxidase-conjugated secondary antibody, the complexes were visualized using an enhanced chemiluminescence kit (DuPont, MA) following the manufacture's instructions.

G. Immunoprecipitation-kinase Activity Assay

Protein extract (50 μg) with or without phospho-amino acid (1 mM final concentration) competitor was incubated with the 4G10 antibody in immunoprecipitation buffer (20 mM Tris, pH 7.5, 150 mM NaCl, 1 mM EDTA, 1 mM EGTA, 1 mM $Na_3VO_4$, 1 mM NaF, 10 mM β-glycerophosphate, 2 μg/mL antipain, 2 μg/mL aprotinin, 2 μg/mL leupeptin, 0.5% Triton X-100, 0.5% Nonidet P-40) at 4° C. for 4 hours on a rocker. About 25 μL packed volume of protein A-agarose was added, and the incubation was continued for another 2 hours. Agarose bead-protein complexes were pelleted by brief centrifugation. After washing with immunoprecipitation buffer three times, 1× SDS sample buffer was added and the sample boiled for 3 minutes. After centrifugation, the supernatant fraction was electrophoresed on 10% SDS-PAGE gel, and the in-gel kinase assay was performed.

RESULTS

A. SA and its Biologically Active Analogues Induce a 48 kDa Protein Kinase.

Figure 1B:
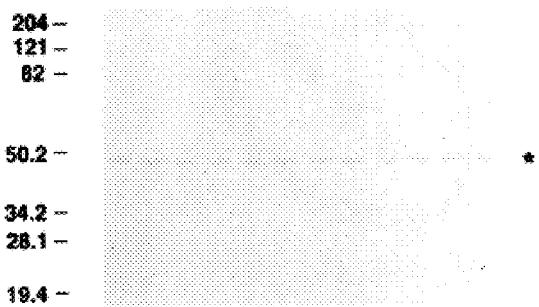
Figure 1C:
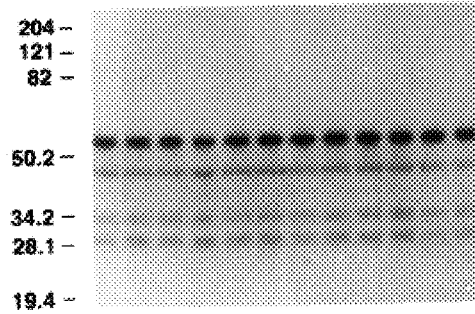
Figure 1D:
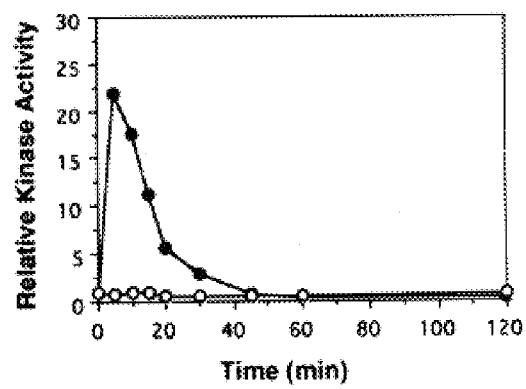
Figure 1E:
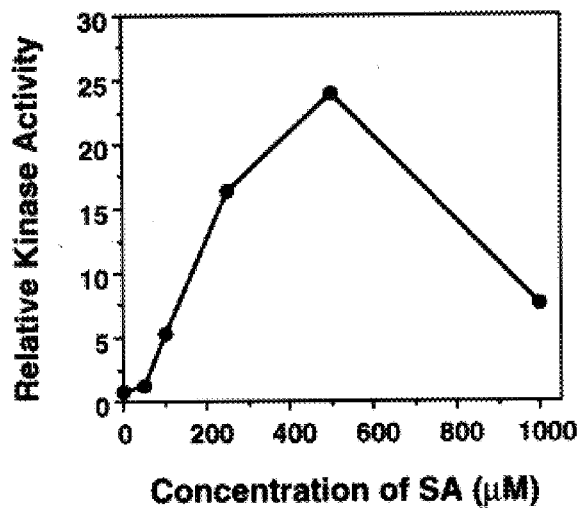

Previous studies have demonstrated that in tobacco, both protein phosphorylation and dephosphorylation are required for the activation of the HR and PR gene expression in response to TMV infection or SA treatment (Conrath et al., 1997; Dunigan and Madlener, 1995). To search for the kinase(s) involved in the pathway, an in-gel kinase activity assay was utilized. Various kinase substrates, including casein, MBP, histone and BSA, were imbedded in the separating gel and kinase activities were tested under different reaction conditions. Treatment of tobacco suspension cells with 250 μM SA activated a 48 kDa kinase that efficiently used MBP as an artificial substrate, as shown in FIG. 1A, while the same kinase was not activated by addition of water, as shown in FIG. 1B. This kinase is called the p48 SIP kinase for SA-induced protein kinase. Activation of the p48 SIP kinase was very rapid and transient, peaking within 5 minutes and returning to basal level in about 45 minutes, then decreasing further thereafter. See FIGS. 1A and 1D. The p48 SIP kinase activity in SA-treated cells increased from 15 to 25 fold in different experiments. The minimum concentration of SA required to activate this p48 kinase was 100 μM under our experimental conditions, with maximum activity obtained at 500 μM (FIG. 1E). When casein, histone, or BSA were used as the substrate, no increases in kinase activities were detected in extracts from SA-treated cells (only casein as substrate is shown in FIG. 1C).

Figure 2:
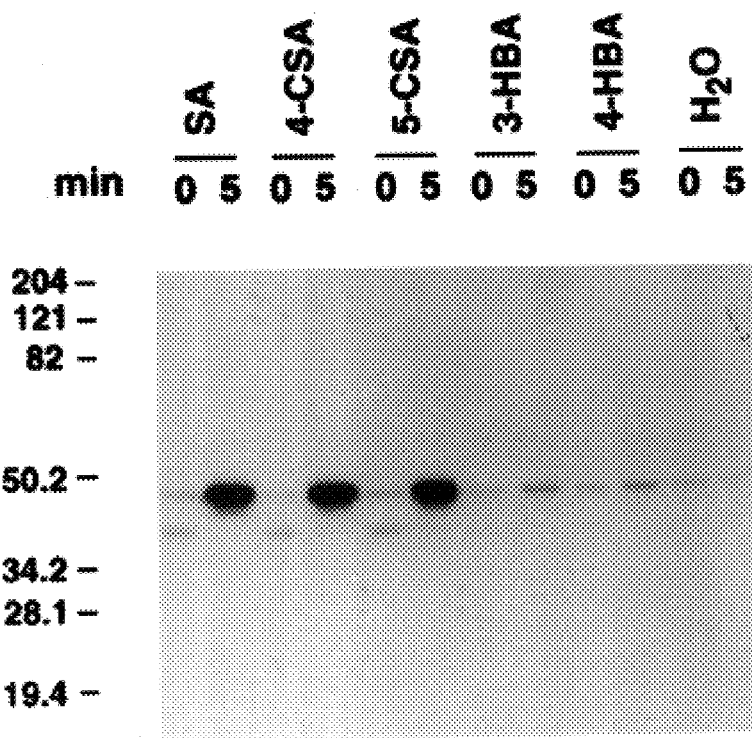
FIG. 2 is an autoradiograph illustrating that only biologically active analogues of SA activate the p48 SIP kinase. Cells were treated with 250 μM of SA or its analogues, 4-chloroSA (4-CSA), 5-CSA, 3-hydroxybenzoic acid (3-HBA), and 4-HBA for 5 minutes. Total cell extracts were prepared, and kinase activities were assayed using MBP as a substrate. The asterisk (*) indicates the position of the p48 SIP kinase. Molecular mass markers at left are given in kDa.

To assess the biological relevance of SA induction of the p48 SIP kinase, analogues of SA were tested. Biologically active analogues of SA, such as 4-chloroSA (4-CSA) and 5-CSA (Conrath et al., 1995) which induce PR gene expression and enhanced disease resistance in tobacco, activated the SIP kinase to similar extents as SA at 250 μM. See FIG. 2. However, both analogues induced a more sustained activation of the SIP kinase than SA (data not shown). This sustained activation may arise due to the inability of these cells to metabolize these compounds efficiently. In contrast, the biologically inactive analogues, 3-hydroxybenzoic acid (3-HBA) and 4-HBA, were poor activators of this kinase as shown in FIG. 2.

B. Hydrogen Peroxide Activates the p48 SIP Kinase, as Well as Several Other Kinases Since $H_2O_2$ is implicated in both the action of SA (Chen et al., 1993) and several defense responses of plants against pathogens (Mehdy, 1994; Levine et al., 1994), the effect of $H_2O_2$ on SIP kinase activity was also examined. As shown in FIG. 3, $H_2O_2$ at 1 mM and 2 mM induced several kinase activities including the p48 SIP kinase. The sizes of the other activated kinases were 58 kDa, 52 kDa, and 40 kDa. Activation of the SIP kinase by $H_2O_2$ was more sustained compared to that induced by SA; even at 60 minutes after addition of $H_2O_2$, kinase activities remained at peak levels.

Figure 4A:
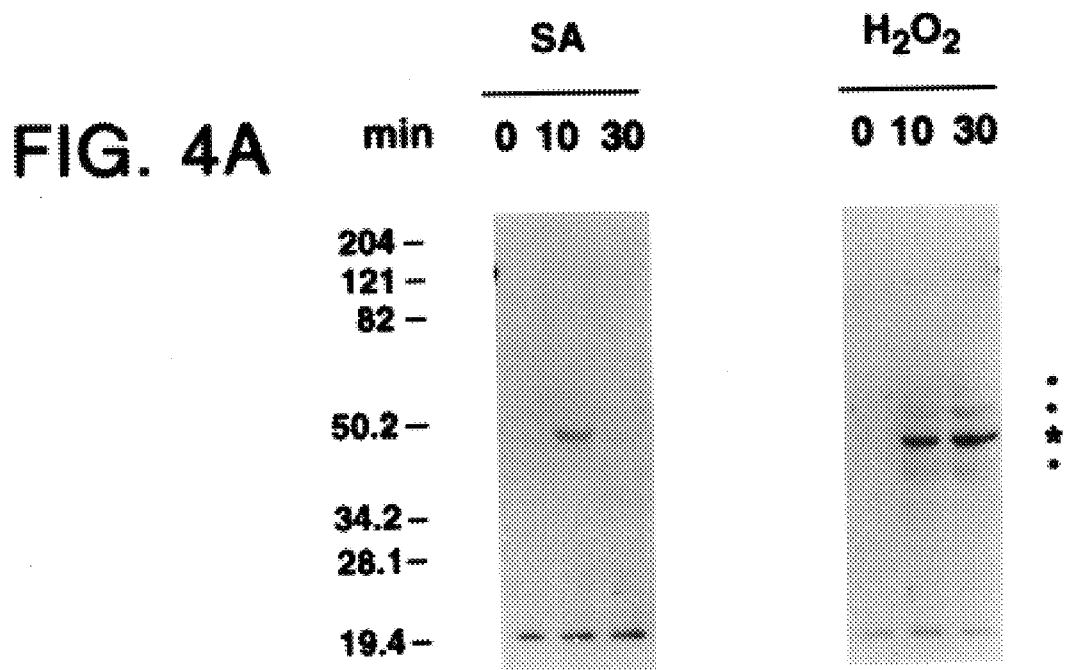
FIGS. 4A and 4B are a pair of autoradiographs showing that activation of the p48 SIP kinase by SA or $H_2O_2$ is associated with phosphorylation of tyrosine residues in the kinase.

C. Activation of the p48 SIP Kinase by SA and $H_2O_2$ is Associated with Phosphorylation of Tyrosine Residue on the Kinase The use of MBP as a preferred substrate suggested that the p48 SIP kinase might be a MAP kinase. Another characteristic of MAP kinases is their activation via simultaneous phosphorylation of tyrosine and threonine residues by MAP kinase kinases (Seger and Krebs, 1995). To determine if the SIP kinase was similarly activated, extracts from SA- or $H_2O_2$-treated cells were subjected to immunoblot analysis using the phosphotyrosine-specific monoclonal antibody 4G10. See FIG. 4A. Increases in the amount of a phosphotyrosine-containing 48 kDa polypeptide were associated with both the SA- and $H_2O_2$-induced activation of the p48 SIP kinase. SA induced a transient activation of the p48 kinase, which correlates with the transient increase in the level of a phosphotyrosine-containing 48 kDa protein. Compare FIG. 1A with FIG. 4A. Hydrogen peroxide induced both sustained activation of the p48 kinase, as shown in FIG. 3, and prolonged phosphorylation of tyrosine residue(s) on a 48 kDa protein, as shown in FIG. 4A. These results suggest that the p48 SIP kinase is a MAP kinase.

Figure 4B:
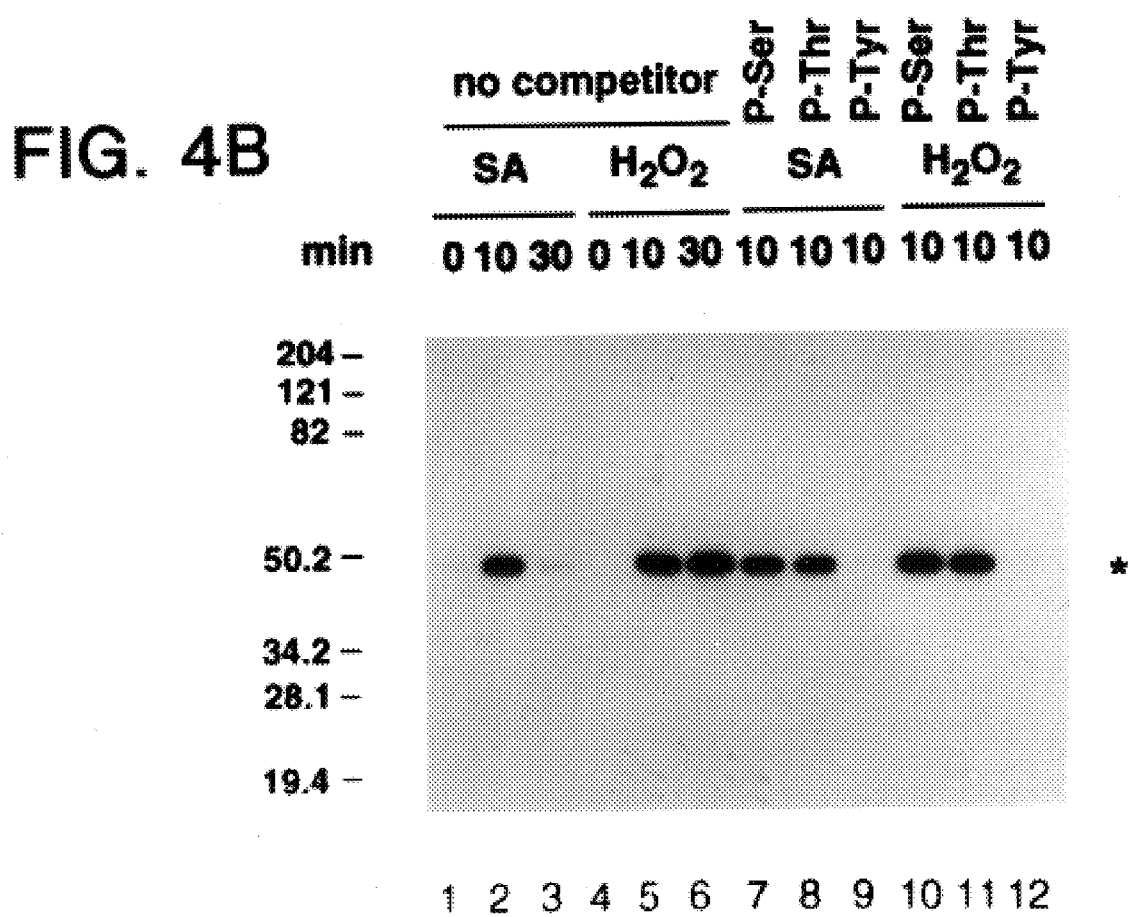

To confirm these results, as well as demonstrate the specificity of the 4G10 monoclonal antibody for phosphotyrosine, immunoprecipitation of phosphotyrosine-containing proteins was coupled with the in-gel kinase activity assay. Phosphotyrosine-containing polypeptides were first immunoprecipitated from extracts of SA- or $H_2O_2$-treated cells and then subjected to the in-gel kinase activity assay. See FIG. 4B. Again, the immunoprecipitated 48 kDa kinase activity, as can be seen in FIG. 4B, lanes 1 to 6, correlates with the p48 SIP kinase activity in the cell extracts (FIGS. 1A and 3), as well as with the amount of a phosphotyrosine-containing 48 kDa protein detected by immunoblot analysis (FIG. 4A). To confirm that the antibody specifically recognized a phosphorylated tyrosine residue in the SIP kinase, phosphoserine, phosphothreonine and phosphotyrosine were used as competitors in the immunoprecipitation experiments described above. See FIG. 4B, lanes 7–12. Only phosphotyrosine inhibited precipitation of the p48 SIP kinase, confirming the specificity of the antibody.

D. Tobacco Leaves Injected with SA have Elevated p48 Kinase Activity

Figure 5A:
FIGS. 5A–5D are a pair of autoradiographs and a pair of graphs showing the induction of p48 SIP kinase following injection of tobacco leaves with SA and/or water.

Activation of the p48 SIP kinase was next monitored in tobacco plants after injection of SA into their leaves. See FIG. 5A and 5C. Injection of 500 μM SA resulted in the rapid activation of a kinase whose activity decreased to basal level in about 30 minutes. This was followed by a second, more prolonged activation of a kinase of the same size which peaked at approximately 3 hours. Using the in-gel kinase assay with crude protein extracts, both activities were observed as a 46 kDa polypeptide, which is the same size as the cutting-induced MAP kinase (termed PMSAP kinase) reported by Usami et al., 1995. However, after immunoprecipitation with the anti-phosphotyrosine monoclonal antibody, both activities migrated as a 48 kDa protein, identical in size to that present in extracts from tobacco suspension cells (data not shown). Coomassie staining of the gel revealed that there was a very abundant protein of about 48 kDa present in leaf but not suspension cell extracts which likely was responsible for the aberrant migration of the p48 kinase activities.

The very rapidly and transiently induced kinase activity was also present in leaves injected with water, suggesting that only the second peak of activity was SA related. See FIG. 5A and 5C. This is consistent with the induction of the first (rapid, transient) peak of activity by biologically inactive as well as active analogues of SA. In contrast, the second peak was induced only by active analogues (data not shown). Thus, the first peak of activity is probably brought about by mechanical and/or osmotic stress.

Figure 5B:
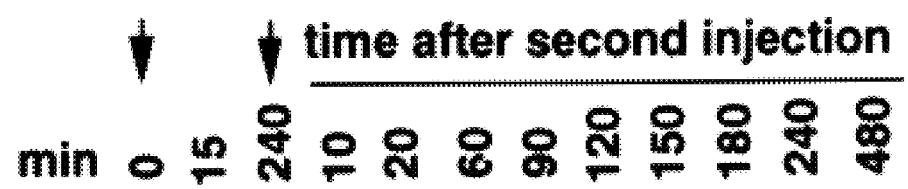
Figure 5B:
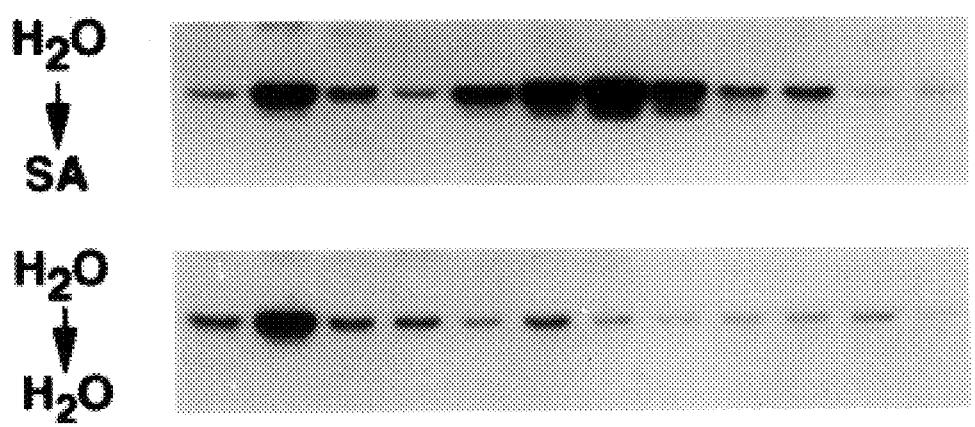
Figure 5C:
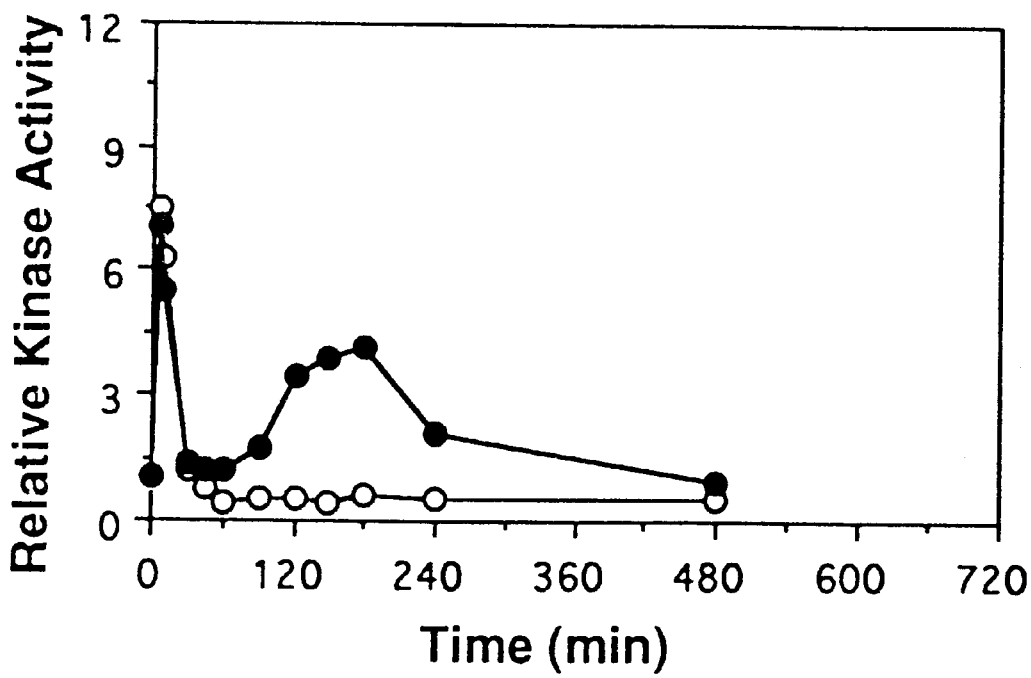
Figure 5D:
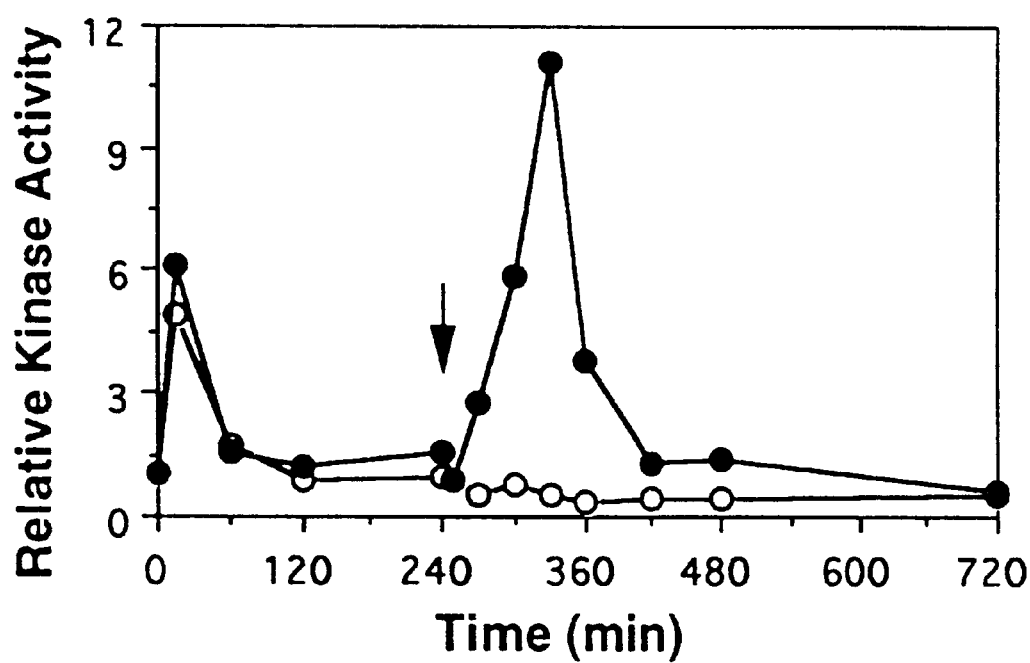

To separate the two kinase activation responses elicited by injection of SA, double-injection experiments were performed. Leaves were first injected with water, and 1, 2 or 4 hours later injected a second time with water or SA. The first injection of water desensitized the mechanical and/or osmotic stress response since a second injection of water failed to activate the 48 kDa kinase again (only the second injection of water at 4 hours is shown in FIG. 5B). In contrast, a second injection of SA led to a dramatic activation of the p48 SIP kinase. This activation occurred more rapidly, was stronger, and less prolonged than the second peak of kinase activity elicited by a single SA injection. Compare FIGS. 5B and 5D with 5A and 5C. It is unclear whether the wounding and/or osmotic stress-induced activity and SA-induced activity were due to the same kinase. The activation of the p48 SIP kinase activity by a second injection of SA, but not of water, in the double-injection experiment suggests that either SIP kinase is distinct from the p48 wounding and/or osmotic stress-induced kinase, or they are the same kinase with different upstream signaling components.

E. TMV Infection Activates the p48 SIP Kinase

Figure 6A:
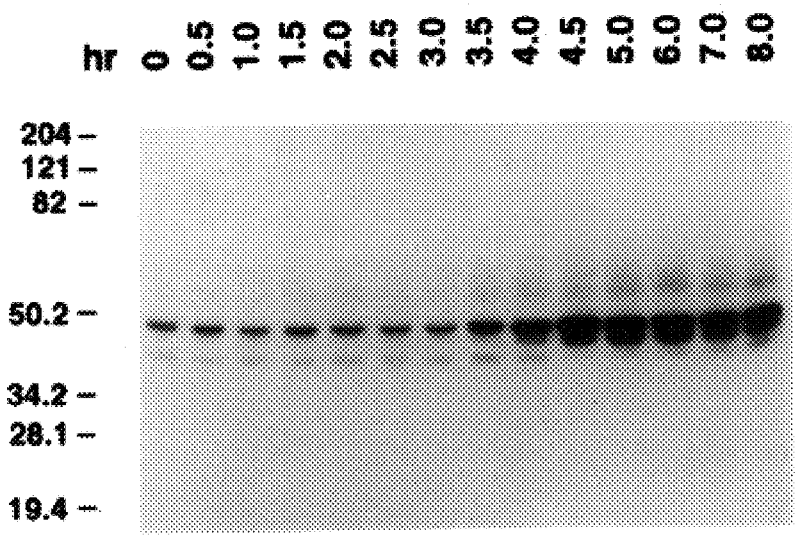
FIGS. 6A–6C depict a pair of autoradiographs, and graph showing that TMV infection of tobacco induces the p48 SIP kinase, along with a p44 kinase. Tobacco leaves were either inoculated with TMV, see FIG. 6A, or mock inoculated, see FIG. 6B. After 48 hours at 32° C. tobacco plants were shifted to 22° C. and leaf discs were collected at the indicated times post shift. Total protein extracts were prepared and kinase activities were assayed with MBP as a substrate.
Figure 6B:
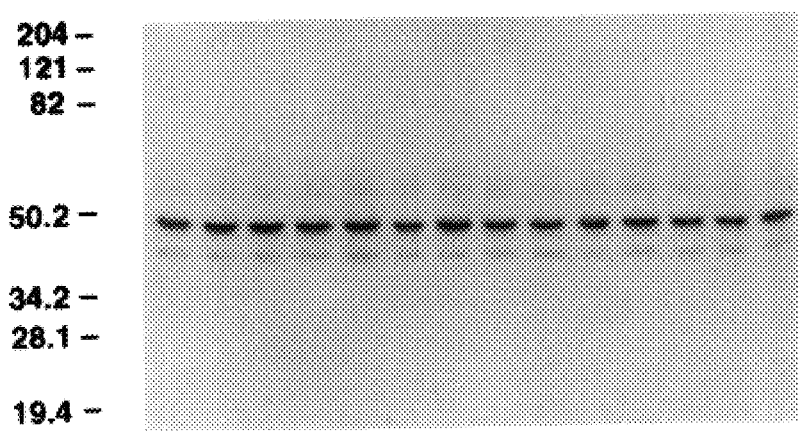
Figure 6C:
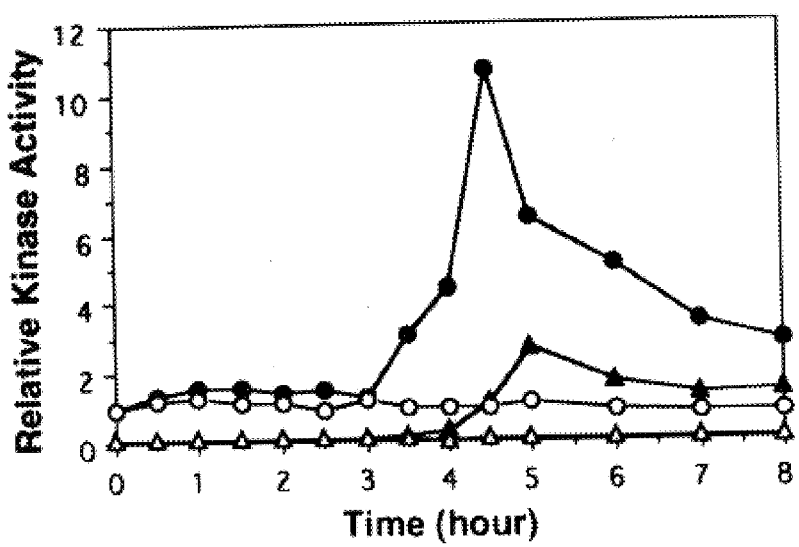

As TMV infection of resistant tobacco plants leads to elevated levels of endogenous SA (Malamy et al., 1992), p48 SIP kinase activity was monitored after TMV infection. To more readily follow changes in kinase activity, advantage was taken of the reversible, high temperature inhibition of defense responses to TMV in resistant tobacco. At 32° C. TMV-infected tobacco fails to (i) produce elevated levels of SA, (ii) synthesize PR proteins, (iii) restrict virus multiplication and spread, and (iv) develop necrotic lesions. Upon shifting these plants to lower temperatures (22° C.) all of the above defense responses are rapidly and strongly induced (Malamy et al., 1992). In the experiments shown here, plants were infected with TMV and then maintained at 32° C. for 48 hours before shifting to 22° C. Under these conditions, SA levels rise several fold between 0 and 4 hours and then 10–50 fold more by 6 hours after the shift (Malamy et al., 1992; Guo and Klessig, unpublished). The increase in p48 SIP kinase activity paralleled the rise in SA. See FIG. 6. Activity of this kinase began to increase at about 3.5 hours, peaked approximately 10 fold above basal level at 4.5 hours, and then declined.

The activity of a second, slightly smaller kinase (approximately 44 kDa) was also induced by TMV infection. See FIG. 6. Its activation was delayed until 4.5 hours and then rose dramatically from an undetectable basal level. Activation of this p44 kinase was also evident after SA treatment of tobacco plants (FIGS. 5A and 5B) but not suspension cells (FIG. 1A). The identity of this kinase is unknown, but based on its substrate preference, it may be another MAP kinase.

EXAMPLE 2

PURIFICATION AND CLONING OF TOBACCO SIP KINASE

In this Example, the purification of the p48 SIP kinase from tobacco is described. The cloning and characterization of a cDNA encoding the tobacco SIP kinase is also described.

MATERIALS AND METHODS
A. Purification of p48 SIP Kinase

All purification procedures were carried out in a cold room or in a 4° C. chamber. Protein extract from about 200 grams of SA-treated cells was first fractionated by $(NH_4)_2SO_4$ precipitation. Saturated ammonium sulfate solution was slowly added to total protein extract to 30% of final concentration. After slowly stirring for 30 minutes, the precipitate was collected by centrifugation at 23,000×g for 10 minutes. The pellets were then dissolved in a total of 30 mL of buffer A (25 mM Tris, pH 7.5, 1 mM EGTA, 10 mM β-glycerolphosphate, 0.1 mM $Na_3VO_4$, 1 mM DTT, 5% glycerol) plus 1 mM phenylmethylsulfonyl fluoride, 5 μg/mL each of antipain, aprotinin, and leupeptin. After centrifugation at 130,000×g for 1 hour, the S130 supernatant was dialyzed against 1000 mL of buffer A for 4 hours in the cold room and loaded onto a 10 mL Q-Sepharose column (two tandemly connected 5 mL HiTrapQ columns) equilibrated with buffer A plus 50 mM NaCl. After washing with 30 mL of buffer A, with 50 mM NaCl, the column was eluted with a 150 mL linear gradient of 50 to 400 mM NaCl in buffer A. The p48 SIP kinase activity eluted at about 250 mM. The pooled fractions were adjusted to 300 mM final concentration of NaCl, and loaded onto a 15 mL phenyl-Sepharose/High Performance column (1.6 cm×7.5 cm) equilibrated with buffer A plus 300 mM NaCl. The column was washed with 50 mL buffer A plus 300 mM NaCl and eluted with 100 mL linear gradient of 0–60% ethylene glycol and 300–0 mM NaCl in buffer A. The active fractions (eluting around 40% ethylene glycol) were pooled and diluted with equal volume of buffer A, and then loaded to a MonoQ HR 5/5 FPLC column equilibrated with buffer A plus 100 mM NaCl. After washing with 5 mL buffer A plus 100 mM NaCl, the column was eluted with 30 mL gradient of 100–400 mM NaCl in buffer A. The pooled fractions containing the p48 SIP kinase (about 3 mL) were adjusted to 10 mM $MgCl_2$ final concentration and diluted with equal volume of buffer B (25 mM Tris, pH 7.5, 10 mM $MgCl_2$, 1 mM EGTA, 1 mM DTT, 10 mM β-glycerolphosphate, 0.1 mM $Na_3VO_4$, and 0.02% Triton X-100). The sample was then loaded onto a MBP-Sepharose affinity column (1 mL) and equilibrated with buffer B plus 50 mM NaCl. The column was step-eluted with 5 mL each of buffer B plus 100 mM NaCl, 500 mM NaCl, and 1000 mM NaCl. The pooled fractions containing the p48 SIP kinase (about 2.5 mL) were diluted with 3 volumes of buffer B and loaded to a 3.5 mL poly-L-lysine-agarose column (0.9 cm×5.5 cm). After washing with buffer B plus 50 mM NaCl, the column was eluted with 50 mL gradient of 50–800 mM NaCl in buffer B. The active fractions were pooled and concentrated with a Centricon concentrator (10,000 molecular weight cut-off, Amicon, Mass.). To determine the native molecular weight or to further purify the p48 SIP kinase, the concentrated sample was loaded onto a Superdex 200 HR 10/30 FPLC column equilibrated with buffer B plus 250 mM NaCl, and the column was eluted with the same buffer at 0.5 mL/min.

B. Assay of Kinase Activity

Unless specifically indicated, assays were performed at room temperature for 20 minutes in a final volume of 15 μl containing 0.5 mg/mL of MBP, 50 μM of γ-$^{32}$P-ATP (about 3000–6000 cpm/pmole), 25 mM Tris pH 7.5, 5 mM $MgCl_2$, 1 mM EGTA, 1 mM DTT, and enzyme. The reaction was terminated by the addition of equal volume of 150 mM $H_3PO_4$. Twenty μL of the mixture was spotted onto an 8-well phosphocellulose filter strip (Pierce, Ill.). After washing with 150 mM $H_3PO_4$ extensively, the phospho-protein was eluted with 0.4 mL of 1 N NaOH, and the radioactivity was determined by liquid scintillation counting. Total cpm in the reaction mixture was also determined in order to calculate the specific activity of the enzyme preparation. One unit of p48 SIP kinase was defined as the amount of enzyme that will catalyze the transfer of 1 pmole of phosphate from ATP to MBP in 1 minute.

C. Identification of Phosphorylated Amino Acids in the Substrates

The procedure followed was identical to that described earlier (Zhang et al., 1993), except that two-dimensional thin-layer electrophoresis was used. Phosphorylated substrates were precipitated using 10% (w/v) TCA. After washing with 10% (w/v) TCA and ethanol, the pellets were hydrolyzed in 6 N HCl for 2 hours at 110° C., dried in a Speed-Vac evaporator, and then dissolved in 10 μL phospho-amino acids standard (1 mg/mL each of L-phosphoserine, L-phosphothreonine and L-phosphotyrosine). The phospho-amino acids were separated by two-dimensional high voltage thin-layer electrophoresis as previously described (Sefton, 1996). The position of the standards was visualized by ninhydrin (0.2% (w/v) in acetone), and the labeled amino acids were detected by autoradiography.

D. Treatment of the p48 SIP Kinase with Phosphatases

The phosphatase inhibitors present in the purified p48 SIP kinase preparation were first removed by dialysis against buffer B lacking β-glycerophosphate and $Na_3VO_4$ in a 0.5-mL 10 K dialysis cassette (Slide-A-Lyzer; Pierce). For treatment with serine/threonine protein phosphatase PP1 (Calbiochem, San Diego, Calif.), $MnCl_2$, DTT, and BSA were added to aliquots of the SIP kinase preparation to final concentrations of 200 μm, 5 mM and 100 μg/mL respectively. Then 0.1 unit of PP1 was added, and the reaction mixture was incubated at 30° C. in the presence or absence of 1 μM of the phosphatase inhibitor okadaic acid (Calbiochem). For treatment with the tyrosine-specific protein phosphatase YOP (Calbiochem), NaCl, DTT, and BSA were added to purified SIP kinase to final concentrations of 150 mM, 5 mM and 100 μg/mL, respectively. Then 0.5 unit of YOP was added, and the reaction was incubated at 30° C. in the presence or absence of 1 mM of the tyrosine phosphatase inhibitor $Na_3VO_4$. Before assaying for the SIP kinase activity, the phosphatase inhibitors were brought to the same final concentration.B.

E. Microsequencing of Internal Tryptic Peptides

The protein in the active fractions eluted from the poly-L-lysine column was concentrated and precipitated with acetone. The pellets were then dissolved in SDS-Laemmli sample buffer and separated on a 10% SDS-polyacrylamide gel. After Coomassie Brilliant Blue R 250 staining, the 48-kDa band was excised and sent to the W.M. Keck Foundation Biotechnology Resource Laboratory (Yale University, New Haven, Conn.) for amino acid composition and sequence analysis. Briefly, for sequence analysis, the p48 SIP kinase was subjected to in-gel digestion with trypsin, and the resultant peptides were separated by reverse-phase HPLC. After determination of molecular mass and purity using matrix-assisted laser desorption ionization (MALDI) mass spectrometry, selected peptides were sequenced using standard methods.

F. Cloning of Tobacco SIP Kinase cDNA

Two primers, 5'-AAYATHTTYGARGTNACNGC-3' and 5'-CKNCCNGGRAANARNGGYTT-3' (where H is A,T and C; K is T and G; N is A, T, C and G; R is A and G; and Y is T and C), which correspond to peptide 1 and peptide 4 (FIG. 14), respectively, were used to amplify by polymerase chain reaction (PCR) the cDNA that was reverse transcribed from poly(A) RNA prepared from tobacco cell suspension culture. A reverse transcription/PCR product of ~600 bp was cloned into pGEM-T vector (Promega) and sequenced. A clone whose deduced amino acid sequence matched the internal peptide 2 and peptide 3 (FIG. 14) was labeled with $\alpha$-$^{32}$P-dCTP and used to screen a tobacco cDNA library under high stringency. Briefly, nylon membranes (Duralon-UV; Stratagene, La Jolla, Calif.), each with $5 \times 10^4$ plaque-forming units, were hybridized at 42° C. for 20 hr in solution containing 20 mM Pipes, pH 6.5, 0.8 M NaCl, 50% formamide, 1% (w/v) SDS, 100 μg/mL denatured salmon sperm DNA, plus $10^6$ cpm/mL of probe. After hybridization, the filters were washed once with 1× SSC (0.15 M NaCl, 0.015 M sodium citrate), 0.1% (w/v) SDS at room temperature, and three times, each for 15 min, with 0.1× SSC, 0.1% (w/v) SDS at 55° C. More than 10 positive clones were obtained by screening ~$10^6$ plaque-forming units. Both strands of the clone containing the longest insert were sequenced using the Sequenase 2.0 kit (Amersham).

RESULTS

A. Purification of SIP Kinase

Figure 7A:
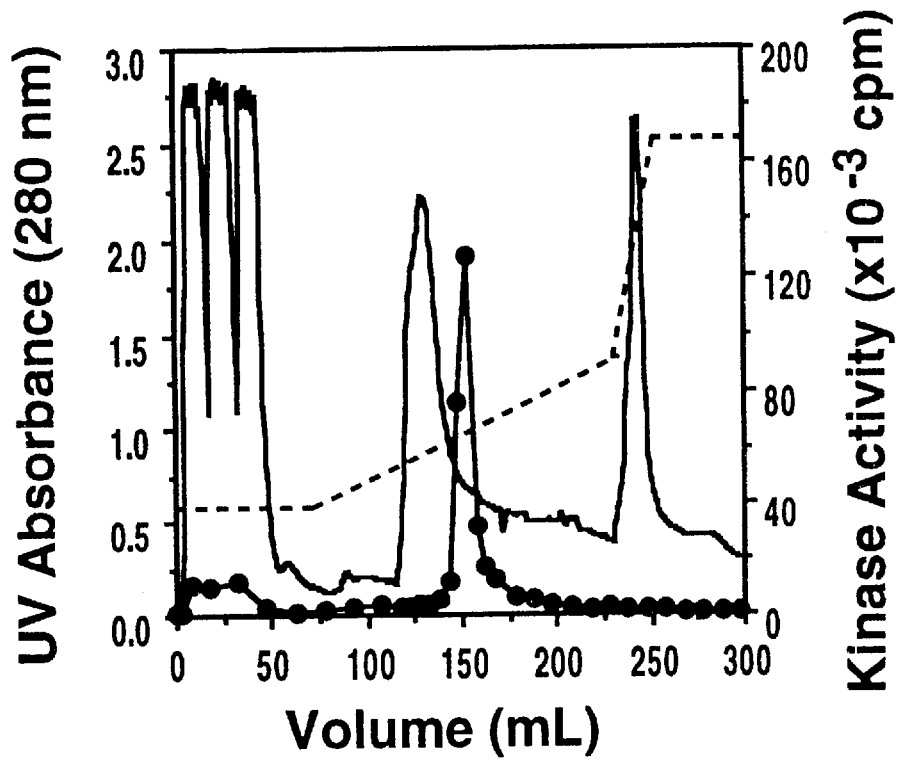
FIGS. 7A–7F depict elution profiles of protein concentration ($A_{280\ nm}$) and kinase activity from each chromatography step in the purification of tobacco SIP kinase, as follows: Q-Sepharose anion exchange column (FIG. 7A); Phenyl-Sepharose HP hydrophobic interaction column (FIG. 7B); MonoQ HR 5/5 anion exchange fast protein liquid chromatography column (FIG. 7C); MBP-Sepharose affinity column (FIG. 7D); Poly-L-lysine-agarose column (FIG. 7E); and Superdex 200 HR 10/30 gel filtration fast protein liquid chromatography column (FIG. 7F). The position of the molecular mass markers in kDa is indicated at the top. Dashed lines indicate the NaCl gradient profiles (as described in Example 2), except in FIG. 7B, where it represents the ethylene glycol gradient. The kinase activity (●) was determined by the in-solution kinase assay, with MBP as substrate.
Figure 7B:
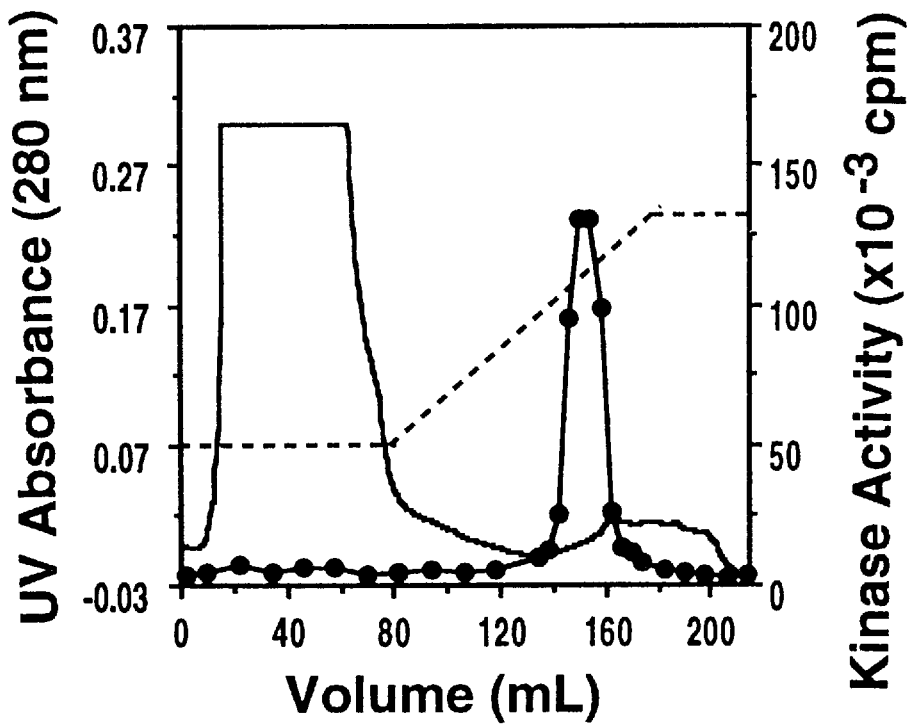
Figure 7C:
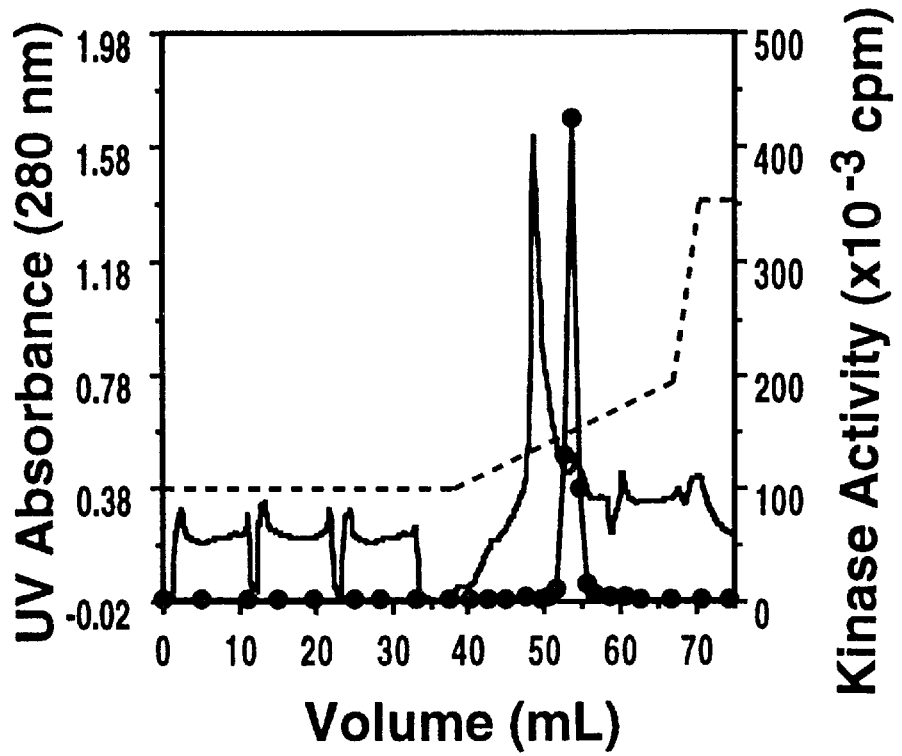
Figure 7D:
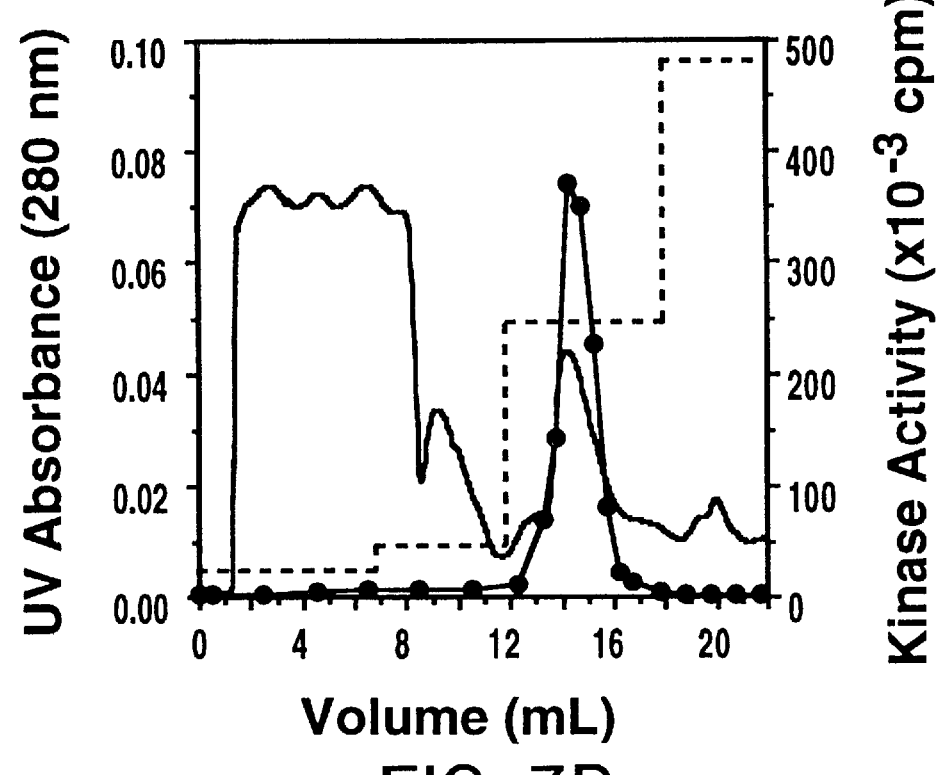
Figure 7E:
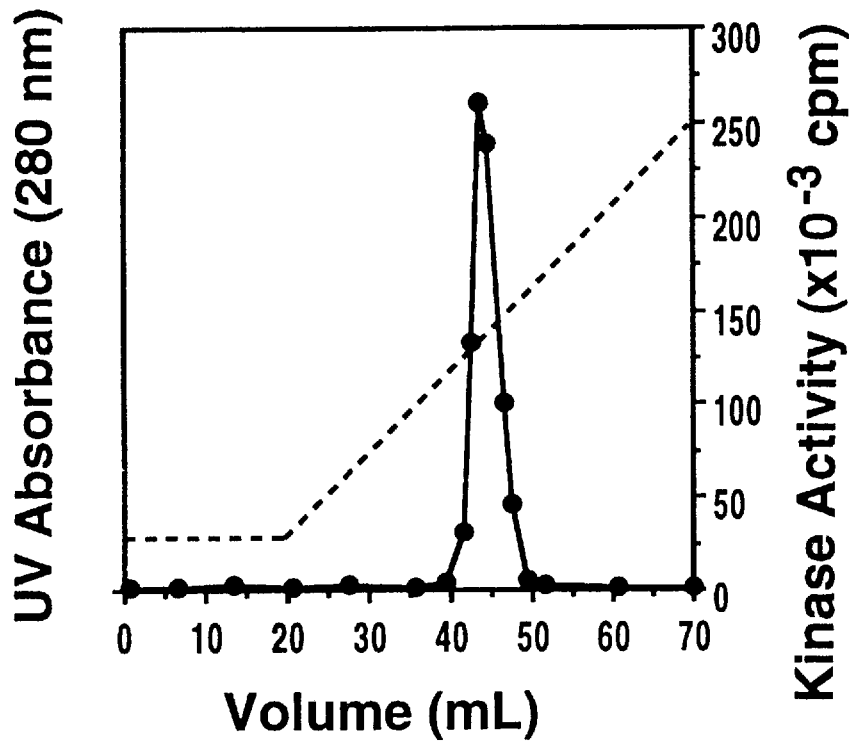
Figure 7F:
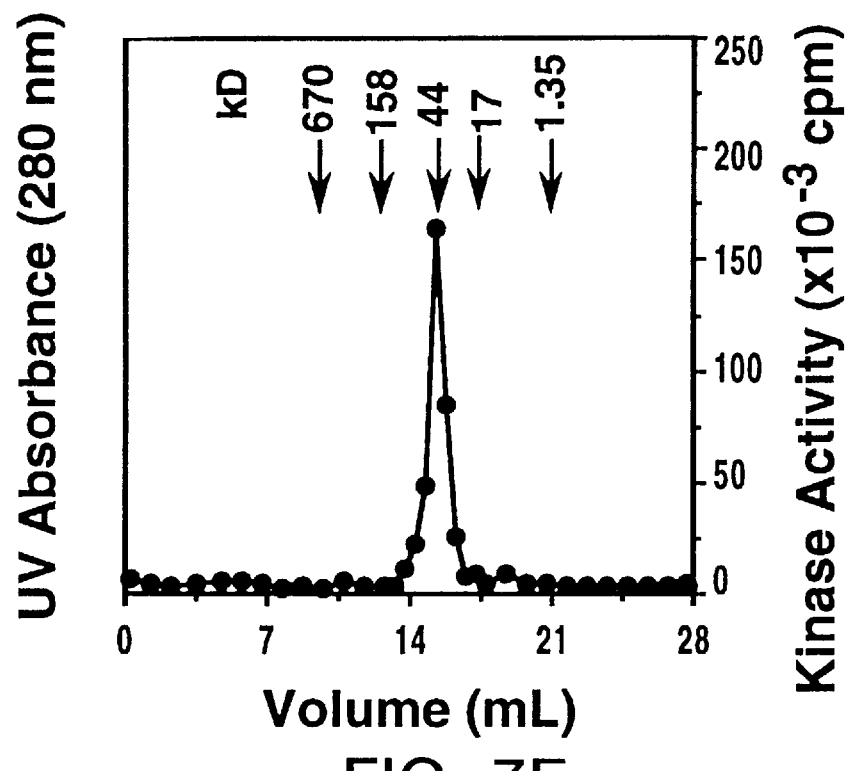
Figure 8A:
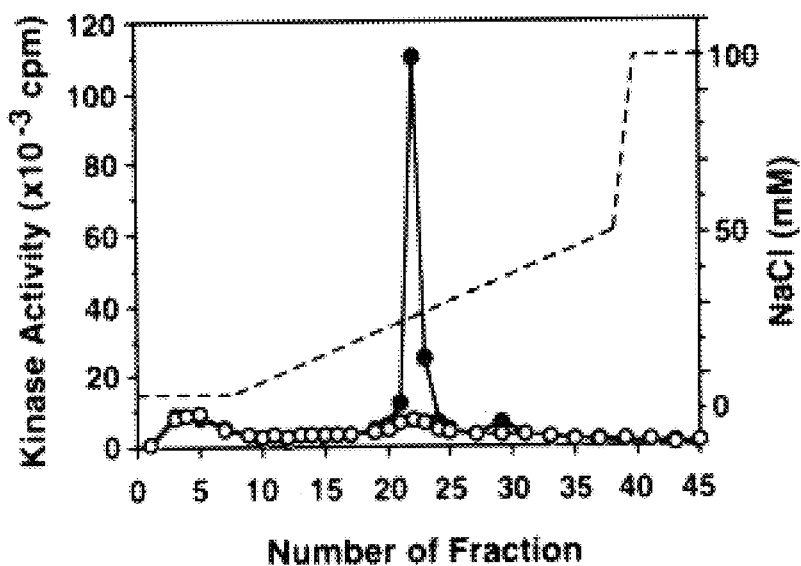
FIGS. 8A and 8B show an elution profile (FIG. 8A) and kinase activity gel (FIG. 8B) illustrating that the major MBP kinase peak eluted from the Q-Sepharose column corresponds to the p48 SIP kinase.
Figure 8B:
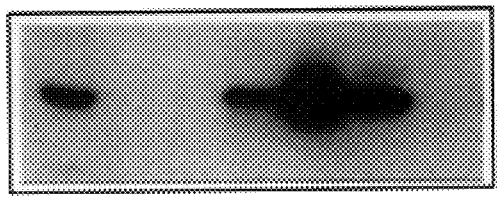

Purification of p48 SIP kinase from SA-treated tobacco suspension cells is summarized in Table I, with typical elution profiles from the column chromatography steps shown in FIG. 7 (FIGS. 7A–7F). The 0 to 30% $(NH_4)_2SO_4$ fraction contained almost all of the p48 SIP kinase activity. Several kinases with similar molecular weight but much lower activity, as determined by the in-gel kinase activity assay, were present in 30% to 75% fractions from both SA-treated and control water-treated cell extracts (data not shown). The 0 to 30% $(NH_4)_2SO_4$ fraction was initially fractionated on a Q-Sepharose anion exchange column (FIG. 7A). The major peak of kinase activity that eluted from this column corresponded to the p48 SIP kinase, based on its absence in the protein preparation obtained from control tobacco cells treated with water (FIG. 8A). Its identity was confirmed by the in-gel kinase activity assay which revealed a major kinase of 48 kDa in the Q-Sepharose fractions with high kinase activity (FIG. 8B). In all of the subsequent chromatographic steps, only a single major kinase activity peak was detected by the in-solution assay using MBP as the substrate (FIG. 7).

Figure 9A:
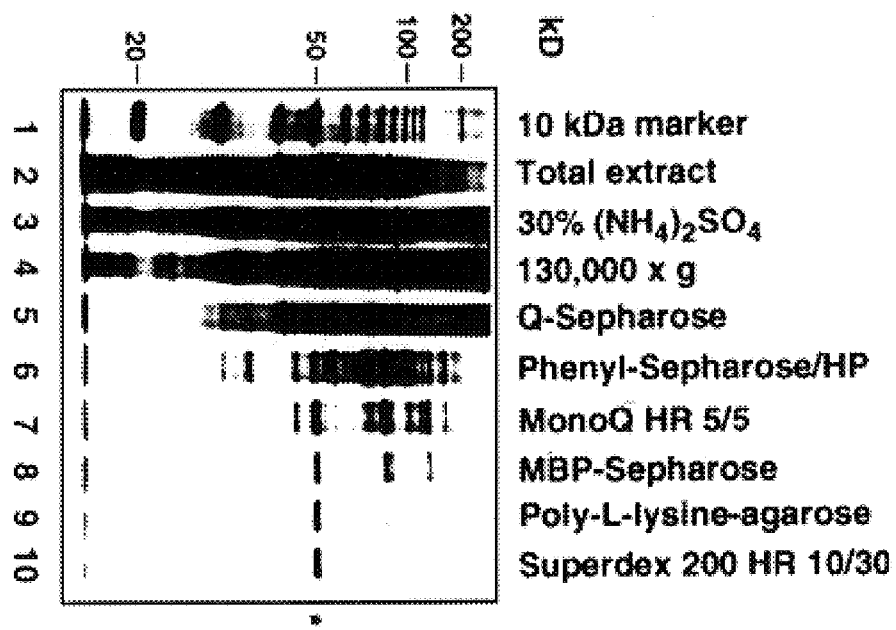
FIGS. 9A–9C show analyses of protein composition (FIG. 9A), the size of the purified kinase (FIG. 9B) and phosphotyrosine-containing polypeptides at different purification steps (FIG. 9C).
Figure 9B:
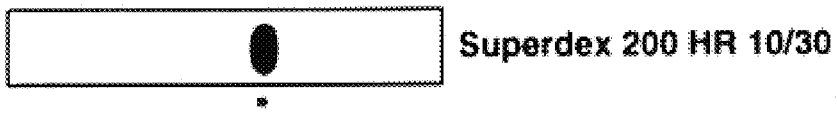
Figure 9C:
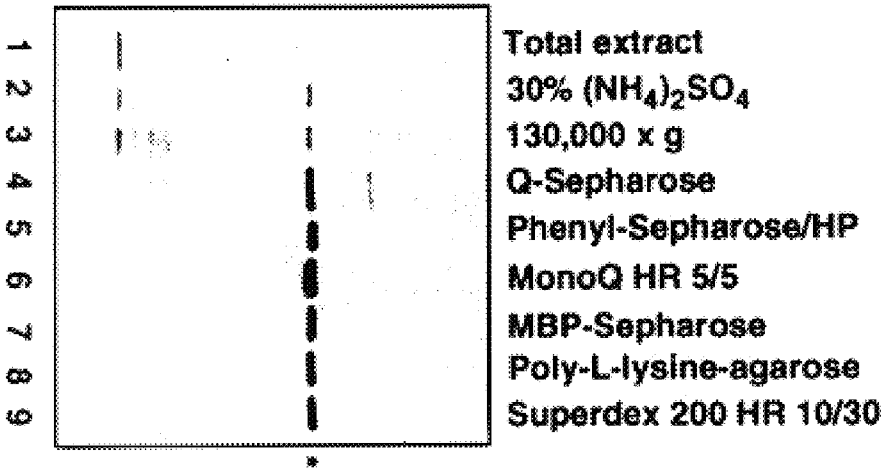

Analysis of the pooled fractions from each purification step by SDS-PAGE revealed that the p48 SIP kinase was purified to apparent homogeneity after the final gel filtration step (FIG. 9A, lane 10). More than 25,000-fold purification was required to obtain enzyme of this purity (Table 1). This result indicated that the p48 SIP kinase was approximately 0.004% of the total soluble protein. The final purified enzyme had a molecular weight of 48 kDa (FIGS. 6A and 6B) and a specific activity of 340 nmol min$^{-1}$ mg$^{-1}$, which is higher than purified MAP kinases obtained from most other sources (Childs and Mak, 1993a and b). To ensure that the 48-kDa band detected on the Coomassie blue-stained SDS-PAGE gels corresponded to the p48 SIP kinase, several precautions were taken. In addition to demonstrating that the p48 SIP kinase activity is present only in protein preparations from SA-treated tobacco cells, we followed the purification of both the 48-kDa band (detected by Coomassie blue-staining of SDS-PAGE gels) and the p48 SIP kinase (monitored by the in-gel activity assay) through the last three steps of purification (data not shown). Their co-purification strongly argues that they are the same protein. Moreover, since the activation of MAP kinases requires phosphorylation of a tyrosine residue in the TXY motif between subdomains VII and VIII of the kinase catalytic domain, the presence of a phosphorylated tyrosine residue in the 48-kDa protein would provide further evidence that it is a MAP kinase. Immunoblot analysis of pooled fractions from each purification step using an anti-phosphotyrosine monoclonal antibody indicated that the 48-kDa polypeptide was heavily phosphorylated on tyrosine residue(s) (FIG. 9C). Furthermore, the enrichment of tyrosine-phosphorylated 48-kDa protein correlated with the purification of p48 SIP kinase activity. Thus, we conclude that the purified 48-kDa protein is the p48 SIP kinase described above.

TABLE I

Purification of the p48 SIP kinase from tobacco suspension culture cells

| Fraction | Protein (mg) | Total Activity (pmol min$^{-1}$) | Specific Activity (pmol min$^{-1}$ mg$^{-1}$) | Recovery (%) | Purification (fold) |
| --- | --- | --- | --- | --- | --- |
| Total extract[a] | 1600 | 20943 | 13.1 | 100 | 1 |
| 30% $(NH_4)_2SO_4$ | 149 | 17082 | 114.6 | 81.6 | 9 |
| 130,000 × g | 116 | 16582 | 142.9 | 79.2 | 11 |
| Q-Sepharose | 12 | 13950 | 1162.5 | 66.6 | 89 |
| Phenyl-Sepharose/HP | 1.482 | 8072 | 5446.7 | 38.5 | 416 |
| MonoQ | 0.572 | 7231 | 12641.6 | 34.5 | 965 |
| MBP-Sepharose | 0.065[b] | 6870 | 105692.3 | 32.8 | 8068 |
| Poly-L-lysine-agarose | 0.030[b] | 5094 | 169800.0 | 24.3 | 12962 |
| Superdex 200 HR 10/30 | 0.005[b] | 1698 | 339600.0 | 8.0 | 25924 |

[a]The starting total extract was prepared from 200 g of cells.
[b]Protein amount estimated by comparing to known standards on Commassie blue-stained SDS-PAGE gel.

B. Characterization of Purified Tobacco p48 SIP Kinase

Figure 10A:
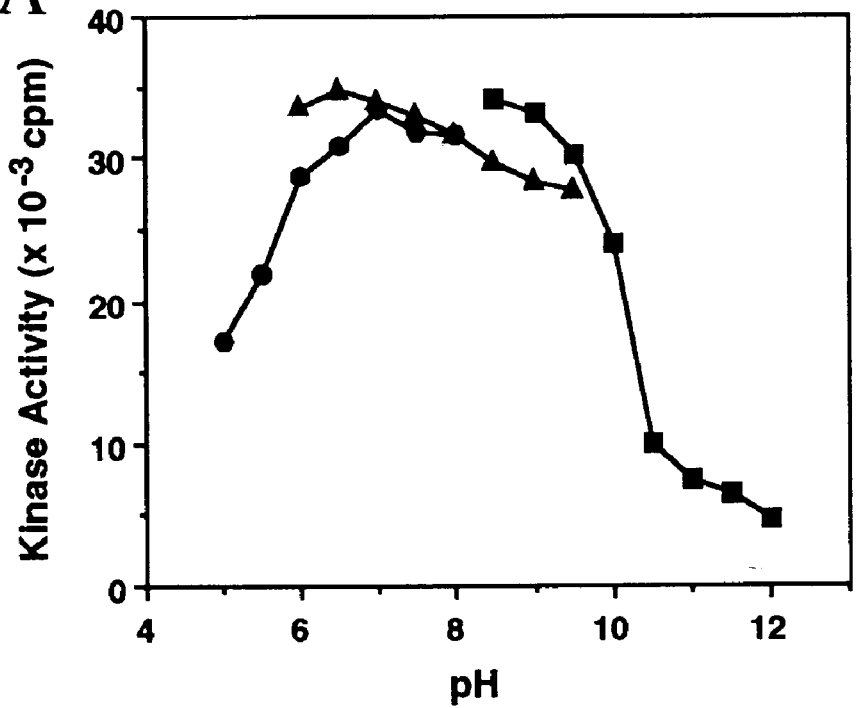
FIGS. 10A and 10B show a pair of graphs illustrating the effect of pH (FIG. 10A), $Mg^{2+}$ and $Mn^{2+}$ (FIG. 10B) on p48 SIP kinase activity. Approximately 0.5 unit of partially purified enzyme was used in each test. Buffers used for measuring the effect of pH were 50 mM 2-[N-morpholino] ethanesulfonic acid (Mes, pH 5.0–8.0, ●), 50 mM Tris (pH 6.0–9.5, ▲), and 50 mM 3-[cyclohexylamino]-1-propanesulfonic acid (Caps, pH 9.0–12.0, ■). For testing the effects of $Mg^{2+}$ (●), and $Mn^{2+}$ (▲), buffer B from the last purification step was first exchanged to $Mg^{2+}$-free buffer using a desalting column. $Mg^{2+}$ was not added in reactions for testing the effect of $Mn^{2+}$.
Figure 10B:
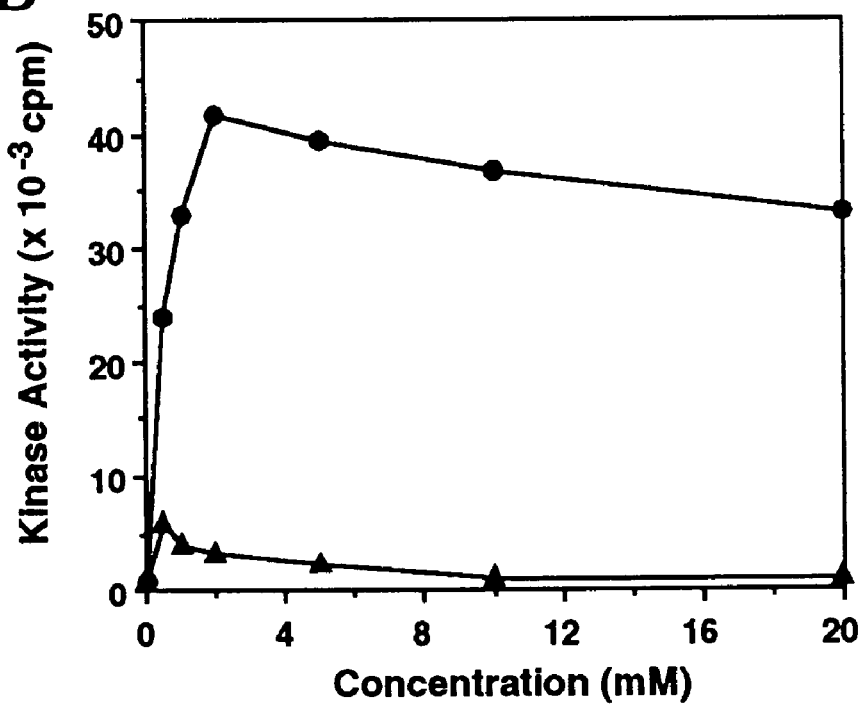
Figure 11:
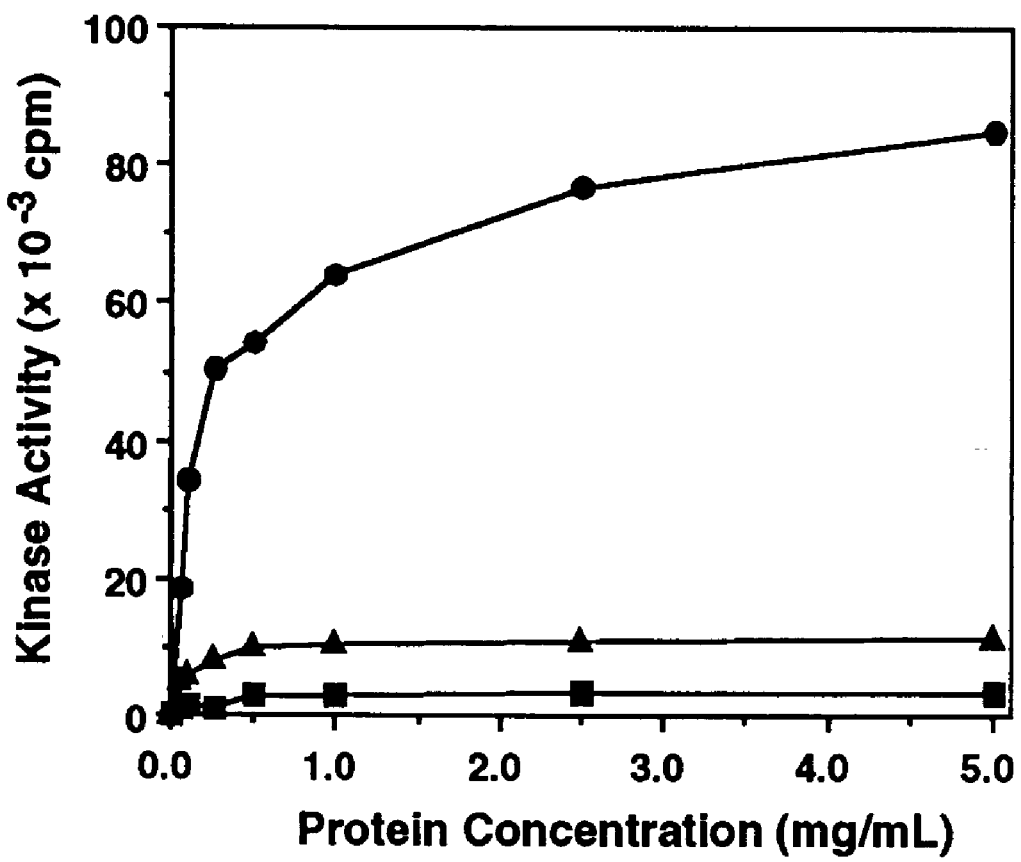
FIG. 11 is a graph depicting the protein substrate preference of the p48 SIP kinase. About 0.5 unit of partially purified enzyme was used in each reaction. The assay conditions were as described below in Example 1, except various concentrations of MBP (●), histone (▲), and casein (■) were used.
Figure 12:
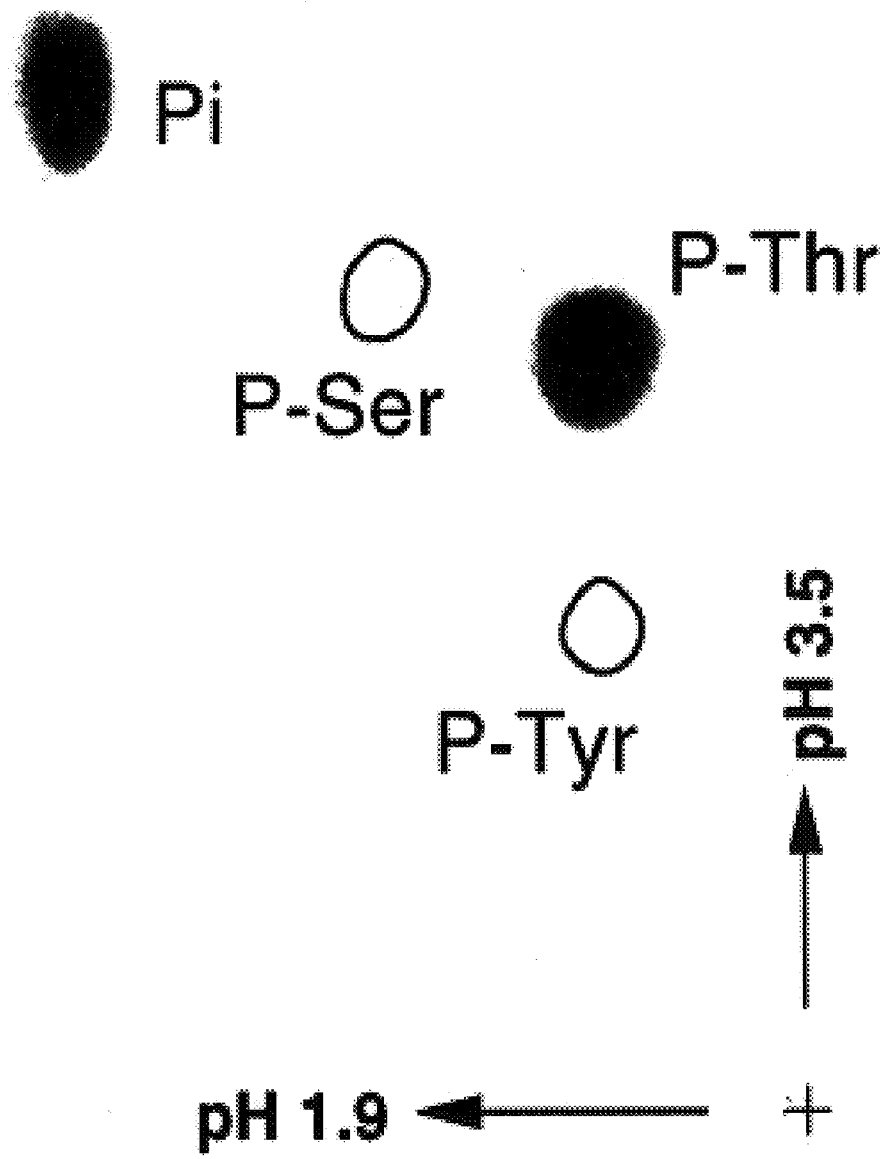
FIG. 12 is an autoradiograph identifying the amino acid phosphorylated by the p48 SIP kinase in MBP. Two and one-half units of partially purified p48 SIP kinase were used to phosphorylate MBP under standard conditions. The reaction was stopped by the addition of 1/10 volume of 100% trichloroacetic acid (TCA). After incubation on ice for 30 minutes, the precipitated protein was collected by centrifugation, and washed with 10% TCA and ethanol. The protein was acid hydrolyzed, and the phospho-amino acid was detected as described below in Example 2.

Purification of the p48 SIP kinase by the protocol outlined in Table 1 through the poly-L-lysine agarose chromatography step removed all other contaminant kinases and therefore allowed the characterization of the p48 SIP kinase by in-solution kinase assay. All further characterization described in FIGS. 10–13, and Table III and IV utilized this partially purified enzyme. The native molecular mass as calculated from size-exclusive FPLC chromatography was 50 kDa (FIG. 7F), which is close to the 48 kDa estimated by SDS-PAGE gel. This result indicates that the p48 SIP kinase is a monomeric enzyme, as are all other MAP kinases. Purified p48 SIP kinase had a very broad optimum pH. See FIG. 10A. Even at pH of 5.5 or 10, it retained more than 50% activity. The enzyme exhibited an absolute requirement for $Mg^{2+}$; $Mn^{2+}$ could not substitute for $Mg^{2+}$. See FIG. 10B. Kinase activity was strongly stimulated by $MgCl_2$ up to a total concentration of 2 mM, and then decrease slightly as the concentration of MgCl$_2$ increase. Stimulation by Mg$^{2+}$ in excess of the amount necessary for the formation of a stable Mg$^{2+}$-ATP complex suggests an additional function for this metal ion. The purified p48 SIP kinase could not use Mg$^{2+}$-GTP as a phospho-donor (data not shown). The absolute Km and Vmax of the enzyme for Mg$^{2+}$-ATP was estimated to be of 24 μM and 0.39 μmole min$^{-1}$ mg$^{-1}$, respectively. See Table II. Of the proteins tested for their ability to serve as in vitro substrates, only MBP proved to be good phosphate acceptor. See FIG. 11. The absolute Km for MBP was 0.19 mg mL$^{-1}$. See Table II. Phospho-amino acid analysis by two-dimensional thin-layer electrophoresis demonstrated that only threonine was phosphorylated on MBP. See FIG. 12.

TABLE II

Structural and kinetic properties of the p48 SIP kinase

| Parameter | Value |
| --- | --- |
| Structural parameters | |
| Native molecular weight[a] | 50,000 |
| Denatured molecular weight[b] | 48,000 |
| Kinetic parameters | |
| Mg$^{2+}$ -ATP | |
| K$_m$ (μM) | 24 |
| V$_{max}$ (μmole min$^{-1}$ mg$^{-1}$) | 0.39 |
| MBP | |
| K$_m$ (mg mL$^{-1}$) | 0.19 |
| V$_{max}$ (μmole min$^{-1}$ mg$^{-1}$) | 0.42 |

[a]Measured relative to internal standards using a Superdex 200 HR 10/30 FPLC column.
[b]Measured relative to known standards by SDS-PAGE.

C. Effectors of p48 SIP Kinase Activity

Under standard assay conditions, none of the compounds tested could significantly stimulate the activity of the partially purified p48 SIP kinase. See Table III. The p48 SIP kinase was very sensitive to the general kinase inhibitor K252a and staurosporine, with I$_{50}$ of 12 nM and 60 nM, respectively. In contrast, EGTA, genistein, protein kinase A peptide inhibitor, and protein kinase C peptide inhibitor had no effect on its activity. See Table III. At high concentrations, both Ca$^{2+}$ and Zn$^{2+}$ inhibited the enzyme. Several poly-ions, including poly-L-Lys, poly-L-Glu, protamine and heparin showed inhibitory effects, while poly-L-Gln and spermidine showed no effect at the concentrations tested. See Table III.

TABLE III

Effects of various reagents on p48 SIP kinase activity

| Reagents | Concentration | Relative Activity % of control[a] |
| --- | --- | --- |
| Kinase Inhibitors | | |
| EGTA | 10 mM | 100 |
| PKA peptide inhibitor | 10 μM | 100 |
| PKC peptide inhibitor | 10 μM | 100 |
| Genistein | 20 μM | 100 |
| K-252a | 12 nM | 50 |
| Staurosporine | 60 nM | 50 |
| Metal ions | | |
| Na$^+$ | 100 mM | 100 |
| Na$^+$ | 750 mM | 50 |

TABLE III-continued

Effects of various reagents on p48 SIP kinase activity

| Reagents | Concentration | Relative Activity % of control[a] |
| --- | --- | --- |
| Ca$^{2+}$ | 0.5 mM | 100 |
| Ca$^{2+}$ | 5.0 mM | 50 |
| Zn$^{2+}$ | 0.10 mM | 100 |
| Zn$^{2+}$ | 0.25 mM | 50 |
| Poly-L-lysine | 25 μg mL$^{-1}$ | 50 |
| Poly-L-glutamate | 500 μg mL$^{-1}$ | 50 |
| Poly-L-glutamine | 500 μg mL$^{-1}$ | 100 |
| Protamine | 25 μg mL$^{-1}$ | 50 |
| Heparin | 50 μg mL$^{-1}$ | 50 |
| Spermidine | 1 mM | 100 |
| SH-modifying compounds | | |
| DTT | 5 mM | 100 |
| Diamide | 5 mM | 50 |

[a]For each reagent, a dose response curve was measured under standard assay conditions. About 0.5 unit of enzyme was used for each reaction. Control was the enzyme activity in the absence of reagent.

Figure 13:
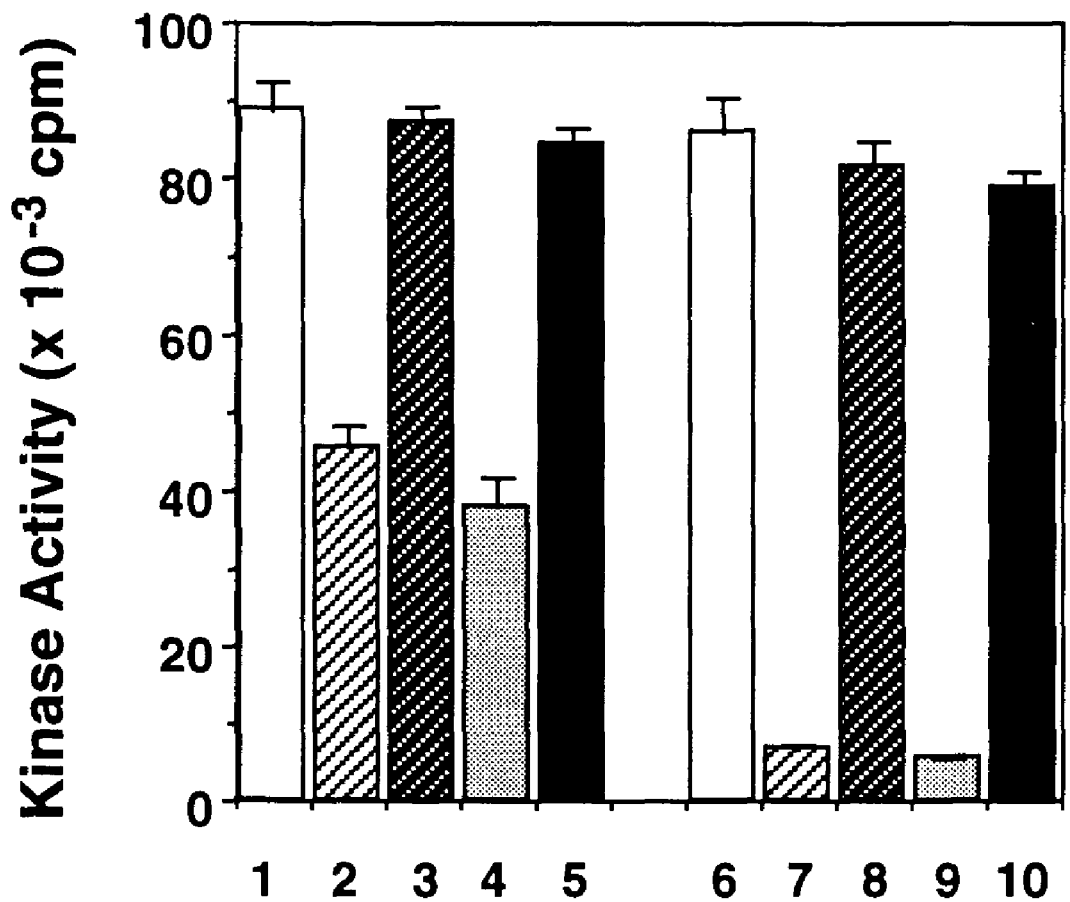
FIG. 13 is a histogram showing inactivation of p48 SIP kinase by phosphatase treatment. Approximately 20 units of the SIP kinase was treated with either the serine/threonine-specific phosphatase PPI (0.1 units) or the tyrosine-specific protein phosphatase YOP (0.5 units) for 10 min (bars 2 to 5) or 30 min (bars 7 to 10) at 30° C. in the presence or absence of a phosphatase inhibitor. Bars 1 and 6 represent the control without phosphatase or phosphatase inhibitor; bars 2 and 7, PPI; bars 3 and 8, PPI plus okadaic acid (1 µM); bars 4 and 9, YOP; bars 5 and 10, YOP plus $Na_3VO_4$ (1 mM). Before assaying for SIP kinase activity, the phosphatase inhibitors were added to all of the reactions to the same final concentrations.

D. Phosphorylation of Both Tyrosine and Serine/threonine Residues are Required for p48 SIP Kinase Activity To assess whether phosphorylation is required for p48 SIP kinase activation, the kinase was treated with either the tyrosine-specific protein phosphatase YOP or the serine/threonine-specific protein phosphatase PP1. Both phosphatases inactivated the SIP kinase (FIG. 13). Furthermore, the inactivation of the SIP kinase by PP1 and YOP, respectively, could be prevented by the addition of okadaic acid, a PP1 inhibitor, or Na$_3$VO$_4$, a tyrosine phosphatase inhibitor. These results confirm that the inactivation of the purified SIP kinase was due to the presence of these phosphatases.

E. Characterization of a cDNA Encoding the Tobacco p48 SIP Kinase

The purified p48 SIP kinase shares several characteristics with MAP kinases, including phosphorylation of a tyrosine residue upon activation, preference for MBP as a substrate, a monomeric structure, and a molecular mass within the range of 38 to 55 kDa. To confirm that SIP kinase is a MAP kinase, partial amino acid sequence was obtained by microsequencing of several internal tryptic peptides (FIG. 14). The sequences from two of the peptides were then used to design primers, and a fragment of the SIP kinase gene was cloned by reverse transcription and PCR amplification. A full-length cDNA clone, which contains all of the peptide sequence obtained by microsequencing of the purified protein (FIG. 14), was obtained by screening of a tobacco cDNA library.

The DNA sequence of the tobacco SIP-kinase cDNA is set forth herein as Sequence I.D. No. 1. The deduced amino acid Sequence (Seq. I.D. No. 2) is shown in FIG. 14. Analysis of these sequences shows that it contains all 11 conserved kinase subdomains found in serine/threonine kinases (Hanks and Hunter, 1995) and has the MAP kinase signature phosphorylation motif TXY preceding subdomain VIII (FIG. 14). The SIP kinase shares 93% amino acid sequence identity with Ntf4 (FIG. 14), a tobacco MAP kinase of unknown function previously isolated by PCR-based homology cloning (Wilson et al., 1995). However, the nucleotide sequence identity of these two genes is only 74%. Although the SIP kinase is definitely a MAP kinase, it differs from all other cloned plant MAP kinases at its N terminus. Furthermore, in conserved subdomain VIII of the kinase catalytic domain, the SIP kinase contains a proline in place of alanine, which is conserved in all other MAP kinases cloned in plants as well as in yeast and mammals.

The SIP kinase is also clearly distinct from WIPK, another member of the tobacco MAP kinase family that has been implicated in the wounding response (Seo et al., 1995). They share only 73% amino acid sequence identity and 51% nucleotide sequence identity. These findings suggest that different MAP kinases are responsible for different stress responses in plants.

REFERENCES

Abe, J.-I., Kusuhara, M., Ulevitch, R. J., Berk, B. C., & Lee, J.-D. (1996) J. Biol. Chem. 271, 16586–16590.
Benhamou, N. (1996) Trends in Plant Science 1, 233–240.
Bokemeyer, D., Sorokin, A., Yan, M., Ahn, N. G., Temleton, D. J., & Dunn, M. J. (1996) J. Biol. Chem. 271, 639–642.
Brumell, J. H., Burkhardt, A. L., Bolen, J. B., & Grinstein, S. (1996) J. Biol. Chem. 271, 1455–1461.
Chang, C., Kwok, S. F., Bleecker, A. B., & Meyerowitz, E. M. (1993) Science 262, 539–544.
Chen, Z., Silva, H., & Klessig, D. F. (1993) Science 262, 1883–1886.
Childs, T. J. & Mak, A. S. (1993a) Biochem. Cell Biol. 71, 544–555.
Childs, T. J. & Mak, A. S. (1993b) Biochem. J. 296, 745–751.
Conrath, U., Chen, Z., Ricigliano, J. R., & Klessig, D. F. (1995) Proc. Natl. Acad. Sci. USA 92, 7143–7147.
Conrath, U., Silva, H., & Klessig, D. F. (1997) Plant J., 11, 747–757.
Dempsey, D. A., & Klessig, D. F. (1995) Bull. Inst. Pasteur 93, 167–186.
Despros, C., Subramaniam, R., Matton, D. P. R. & Brisson, N. (1995) Plant Cell 7, 589–598.
Dietrich, A., Mayer, J. E. & Hahlbrock, K. (1990) J. Biol. Chem. 265, 6360–6368.
Dunigan, D, D, & Madlener, &. C. (1995) Virology 207, 460–466.
Duerr, B., Gawienowski, M., Ropp, T., & Jacobs, T. (1993) Plant Cell 5, 87–96.
Durner, J., & Klessig, D. F. (1995) Proc. Natl. Acad. Sci. USA 92, 11312–11316.
Durner, J., & Klessig, D. F. (1996) J. Biol. Chem., in press.
Felix, G., Grasskapf, D. G., Regenass, M. & Boller, T. (1991) Proc. Natl. Acad. Sci. USA 88, 8831–8834.
Fialkaw, L., Chan, C. K., Rotin, D., Grinstein, S., & Downey, G. P. (1994) J. Biol. Chem. 269, 31234–31242.
Green, R., & Fluhr, R. (1995) Plant Cell 7, 203–212.
Groom, L. A., Sneddan, A. A., Alessi, D. R., Dowd, S., & Keyse, S. M. (1996) EMBO J. 15, 3621–3632.
Gupta, S., Barrett, T., Whitmarsh, A. J., Cavanagh, J., Sluss, H. K., Derijard, B. & Davis, R. J. (1996) EMBO J. 15, 2760–2770.
Guyton, K. Z., Liu, Y., Goraspe, M., Xu, Q., & Holbrook, N. J. (1996) J. Biol. Chem. 271, 4138–4142.
Halliwell, B., Aeschbach, R., Loliger, J., & Aruoma, O. I. (1995) Food Chem. Toxic. 33, 601–617.
Herskowitz, I. (1995) Cell 80, 187–197.
Hunter, T. (1995) Cell 80, 225–236.
John, M., Rohrig, H., Schmidt, J., Walden, R., and Schell, J. (1997) Trends in Plant Science 2, 111–115.
Janak, C., Pay, A., Bogre, L., Hirt, H., & Heberle-Bors, E. (1993) Plant J. 3, 611–617.
Jonak, C., Kiegerl, S., Ligterink, W., Barker, P. J., Huskisson, N. S. & Hirt, L. (1996) Proc. Natl. Acad. Sci. USA 93, 11274–11279.
Kangasjarvi, J., Talvinen, J., Utriainen, M., & Karjalainen, R. (1994) Plant, Cell & Environ. 17, 783–794.
Keyse, S. M. (1995) Biochim. Biophys. Acta 1265, 152–160.
Kieber, J. J., Rothenberg, M., Romam, G., Feldmann, K. A., & Ecker, J. R. (1993) Cell 72, 427–441.
Klessig, D. F. & Malamy, J. (1994) Plant Mol. Biol. 26, 1439–1458.
Knetsch, M. L. W., Wang, M., Snaar-Jagalska, B. E., & Heimovaara-Dijkstra, S. (1996) Plant Cell 8, 1061–1067.
Kyriakis, J. M. & Avruah, J. (1996) BioEssays 18, 567–577.
Levine, A., Tenhaken, R., Dixon, R., & Lamb, C. (1994) Cell 79, 583–593.
Lo, Y. Y. C., Wong, J. M. S., & Cruz, T. F. (1996) J. Biol. Chem. 271, 15703–15707.
Martin, G. B., Brommonschenkel, S. H., Chunwongse, J., Frary, A., Ganal, M. W., Spivey, R., Wu, T., Earle, E. D., & Tanksley, S. D. (1993) Science 262, 1432–1436.
Mehdy, M. C. (1994) Plant Physiol. 105, 467–472.
Mizoguchi, T., Hayashida, N., Yamaguchi-Shinozaki, K., Kamada, H., & Shinozaki, K. (1993) FEBS Lett. 336, 440–444.
Mizoguchi, T., Gotoh, Y., Nishida, E., Yamaguchi-Shinozaki, K., Hayashida, N., Iwasaki, T., Kamada, H., & Shinozaki, K. (1994) Plant J. 5, 111–122.
Mizoguchi, T., Irie, K., Hirayama, T., Hayashida, N., Yamaguchi-Shinozaki, K., Matsumota, K., & Shinozaki, K. (1996) Proc. Natl. Acad. Sci. USA 93, 765–769.
Nishihama, R., Banno, H., Shibata, W., Hirano, K., Nakashima, M., Usami, S. & Machida, Y. (1995) Plant Cell Physiol. 36, 749–757.
Ricci, P., Bonnet, P., Huet, J. C., Sallantin, M., Beauvais-Cante, F., Bruneteau, M., Billard, V., Michel, G., and Pernollet, J. C. (1989) Eur. J. Biochem. 183, 555–563.
Ryals, J., Uknes, S., & Ward, E. (1994) Plant Physiol. 104, 1109–1112.
Ryals, J., Neuenschwander, U. H., Willits, M. G., Molina, A., Steiner, H.-Y., & Hunt, M. D. (1996) Plant Cell 8, 1809–1819.
Seger, R. & Krebs, E. G. (1995) FASEB J. 9, 726–735.
Seo, S., Okamoto, M., Seto, H., Ishizuka, K., Sano, H., & Ohashi, Y. (1995) Science 270, 1988–1992.
Stone, J. M. & Walker, J. C. (1995) Plant Physiol 108, 451–457.
Sundaresan, M., Yu, Z.-X., Ferrans, V. J., Irani, K., & Finkel, T. (1995) Science 270, 296–299.
Suzuki, K. & Shinshi, H. (1995) Plant Cell 7, 639–647.
Usami, S., Banno, H., Ito, Y., Nishihama, R. & Machida, Y. (1995) Proc. Natl. Acad. Sci. USA 92, 8660–8664.
Viard, M.-P., Martin, F., Pugin, A., Ricci, P. & Blein, J.-P. (1994) Plant Physiol. 104, 1245–1249.
Vojtek, A. B., & Cooper, J. A. (1995) Cell 82, 527–529.
Wilson, C., Anglmayer, R., Vicente, O., and Heberle-Bors, E. (1995) Eur. J. Biochem. 233, 249–257.
Yang, Y., Shah, J., and Klessig, D. (1997) Genes & Devel., in press.
Zhang, S., Jin, C.-D., & Roux, S. J. (1993) Plant Physiol. 103, 955–962.
Zhou, J., Loh, Y. T., Bressan, R. A., & Martin, G. B. (1995) Cell 83, 925–935.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated nucleic acid molecule that includes an open reading frame encoding a MAP kinase protein, said protein being activated by an agent that induces a disease defense response in plants, wherein said open reading frame encodes Sequence I.D. No. 2.

2. The nucleic acid molecule of claim 1, which comprises Sequence I.D. No. 1.

3. A recombinant DNA molecule comprising the nucleic acid molecule of claim 1, operably linked to a vector for transforming cells.

4. An isolated single stranded or double stranded nucleic acid molecule having a sequence selected from the group consisting of:
   a) Sequence I.D. No. 1;
   b) an allelic variant of Sequence I.D. No. 1; and
   c) a sequence encoding a polypeptide having amino acid Sequence I.D. No. 2.

5. A recombinant DNA molecule comprising the nucleic acid molecule of claim 4, operably linked to a vector for transforming plant cells.

6. A plant cell transformed with the recombinant DNA molecule of claim 3.

7. A transgenic plant comprising the recombinant DNA molecule of claim 3.

8. A plant cell transformed with the recombinant DNA molecule of claim 5.

9. A transgenic plant comprising the recombinant DNA molecule of claim 5.

10. An isolated nucleic acid molecule that encodes a salicylic acid-activated MAP kinase protein having SEQ ID NO:2, or an allelic variant thereof.

* * * * *

UNITED STATES PATENT AND TRADEMARK OFFICE
CERTIFICATE OF CORRECTION

PATENT NO : 5,977,442
DATED : November 2, 1999
INVENTOR(S): Daniel F. Klessig and Shuqun Zhang It is certified that error appears in the above-identified patent and that said Letters Patent are hereby corrected as shown below:

Please correct the name of applicant in column 19, line 75 to read Shuqun Zhang, as evidenced by the Declaration and Official Filing Receipt.

Signed and Sealed this

Seventeenth Day of April, 2001

*Attest:*

NICHOLAS P. GODICI

*Attesting Officer*     *Acting Director of the United States Patent and Trademark Office*